US011198704B2

(12) United States Patent
Chae et al.

(10) Patent No.: US 11,198,704 B2
(45) Date of Patent: Dec. 14, 2021

(54) BUTANE-TETRAOL-BASED AMPHIPHILES AND USES THEREOF

(71) Applicant: Industry-University Cooperation Foundation Hanyang University Erica Campus, Ansan-si (KR)

(72) Inventors: Pil Seok Chae, Ansan-si (KR); Manabendra Das, Kaiserslautern (DE)

(73) Assignee: Industry—University Cooperation Foundation Hanyang University Erica Campus, Yeonsu-gu (KR)

( * ) Notice: Subject to any disclaimer, the term of this patent is extended or adjusted under 35 U.S.C. 154(b) by 0 days.

(21) Appl. No.: 16/323,786

(22) PCT Filed: Feb. 10, 2017

(86) PCT No.: PCT/KR2017/001478
§ 371 (c)(1),
(2) Date: Feb. 7, 2019

(87) PCT Pub. No.: WO2018/030602
PCT Pub. Date: Feb. 15, 2018

(65) Prior Publication Data
US 2020/0123187 A1   Apr. 23, 2020

(30) Foreign Application Priority Data
Aug. 10, 2016 (KR) ........................ 10-2016-0101972

(51) Int. Cl.
| | | |
|---|---|---|
| C07H 15/04 | (2006.01) | |
| C07K 1/14 | (2006.01) | |
| C07K 14/38 | (2006.01) | |
| C07K 14/705 | (2006.01) | |

(52) U.S. Cl.
CPC ............. *C07H 15/04* (2013.01); *C07K 1/145* (2013.01); *C07K 14/38* (2013.01); *C07K 14/70571* (2013.01)

(58) Field of Classification Search
CPC ........ C07H 15/04; C07K 1/145; C07K 14/38; C07K 14/70571
See application file for complete search history.

(56) References Cited

U.S. PATENT DOCUMENTS 5,811,405 A   9/1998 Toepfer et al.

FOREIGN PATENT DOCUMENTS

| CA | 2144388 A1 | * | 9/1995 | ............. A61P 31/04 |
|---|---|---|---|---|
| EP | 0671408 | | 9/1995 | |
| WO | WO 2018/030602 | | 2/2018 | |

OTHER PUBLICATIONS

International Search Report and the Written Opinion dated May 19, 2017 From the International Searching Authority Re. Application No.PCT/KR2017 i0014 78 and Its Translation of Search Report Into English. (8 Pages).
Chemical Abstract Chemical Abstract Compound, SIN Express, RN 1053747-71-9, Sep. 28, 2008.
Das et al. "Butane-1,2,3,4-Tetraol-Based Amphiphilic Stereoisomers for Membrane Protein Study: Importance of Chirality in the Llinker Region†", Chemical Science.8: 1169-1177, Oct. 5, 2016.
Das et al. "Comparative Study on Diastereomeric Amphiphiles for Membrane Protein Study", Proceedings of KCS 117th General Meetings, Apr. 20, 2016, 56(4): 1-2, Apr. 20, 2016.
Ehsan et al. "Highly Branched Pentasaccharide-Bearing Amphiphiles for Membrane Protein Studies", Journal of the American Chemical Society, 138(11):3789-3796, Mar. 11, 2016.
Vaino et al. "Synthesis of 1,2,3-tri-O-/3-Lactosyl-D-Threitol and 1-O-Benzyl-2,3,4-tri- O-/3- Lactosyl-D-threitol 1", Carbohydrate Research 305: 27-31, 1998.

* cited by examiner

*Primary Examiner* — Jonathan S Lau

(57) ABSTRACT

A newly developed butane-tetraol-based amphiphilic compound, a method of preparing the same, and a method of extracting, solubilizing, stabilizing, crystallizing or analyzing a membrane protein using the amphiphilic compound are provided. The butane-tetraol-based compound is found to have a central structure exhibiting chirality, and isomers of the compound have clearly different characteristics according to the stereochemistry of the central structure, thereby making it possible to select compounds suitable for the uses thereof. Also, the compound can be used to effectively extract a membrane protein, which has more various structures and characteristics than conventional compounds, from cell membranes and stably store the membrane protein in an aqueous solution for a long time, and thus analyze the function and structure of the membrane protein. The analysis of the structure and function of the membrane protein is one of the fields which have received the most attention in biology and chemistry since the analysis of the structure and function of the membrane protein is closely associated with the development of new drugs.

14 Claims, 13 Drawing Sheets

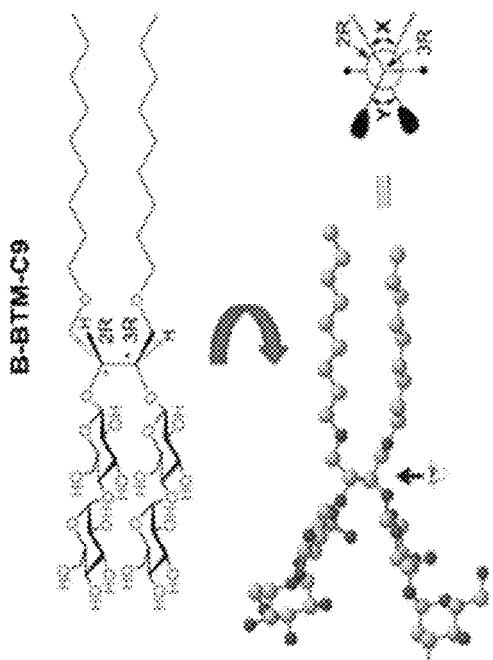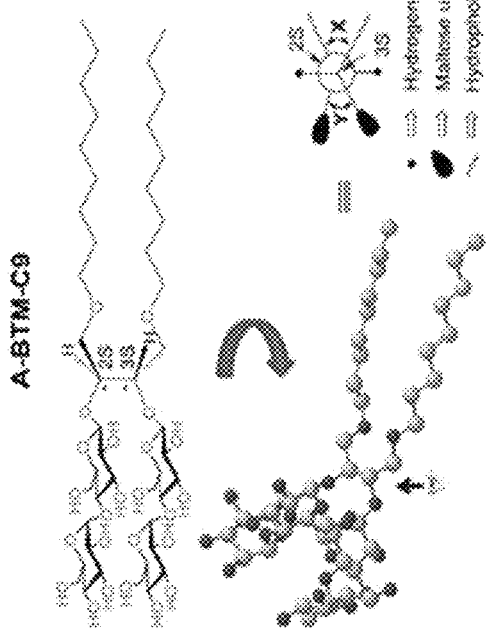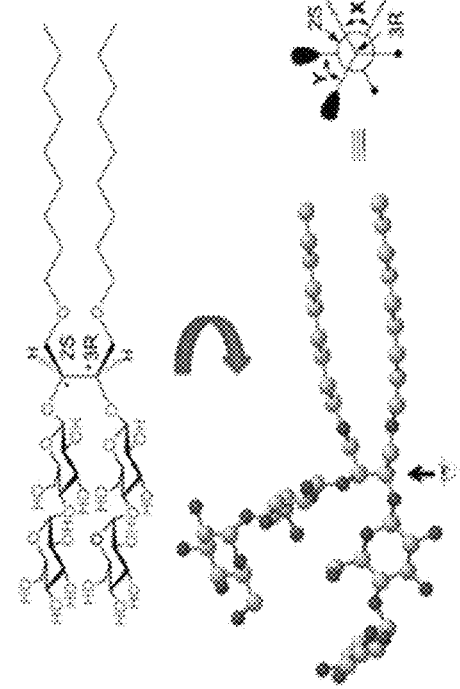
FIG. 6A FIG. 6B FIG. 6C FIG. 6D

BUTANE-TETRAOL-BASED AMPHIPHILES AND USES THEREOF

RELATED APPLICATIONS

This application is a National Phase of PCT Patent Application No. PCT/KR2017/001478 having International filing date of Feb. 10, 2017, which claims the benefit of priority of Korean Patent Application No. 10-2016-0101972 filed on Aug. 10, 2016. The contents of the above applications are all incorporated by reference as if fully set forth herein in their entirety.

FIELD AND BACKGROUND OF THE INVENTION

The present invention relates to a newly developed butane-tetraol-based amphiphilic compound, a method of preparing the same, and a method of extracting, solubilizing, stabilizing, crystallizing or analyzing a membrane protein using the amphiphilic compound.

Membrane proteins play an important role in biological systems. Because these bio-macromolecules include hydrophilic and hydrophobic moieties, amphiphilic molecules are required to extract membrane proteins from cell membranes and solubilize and stabilize the membrane proteins in an aqueous solution.

High-quality crystals of a membrane protein should be obtained to analyze a structure of the membrane protein. For this purpose, the structural stability of the membrane protein in the aqueous solution should take precedence. There are over one hundred conventional amphiphilic molecules that have been used for membrane protein research. However, among these, five amphiphilic molecules have been actively used to conduct research on the structure of the membrane protein. The five amphiprotic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (S. Newstead et al., Protein Sci. 17 (2008) 466-472., Newstead et al., Mol. Membr. Biol. 25 (2008) 631-638.). However, since many membrane proteins surrounded by these molecules tend to be easily structurally denatured or condensed to rapidly lose their functions, there are many limitations in research on the function and structure of the membrane protein using these molecules. This is because the conventional molecules exhibit various characteristics due to their simple chemical structures. Therefore, there is a need to develop novel amphiprotic materials having new excellent characteristics through novel structures.

Meanwhile, high-quality crystals of a membrane protein should be obtained to analyze the structure of the membrane proteins. For this purpose, the structural stability of the membrane protein in the aqueous solution should take precedence. So far, there is no research on the membrane protein conducted using an amphiphilic stereoisomer. However, since the proteins themselves exhibit chirality, and micelles having a self-assembled structure of an amphiphilic molecule have greatly varying characteristics due to the chirality of the amphiphilic molecule as a component, the chirality of the amphiphilic molecule is considered to play an important role in stabilization and crystallization of the membrane protein.

Accordingly, the present inventors have developed an amphiphilic compound as a chiral stereoisomer by introducing a hydrophobic group and a hydrophilic group to a central structure exhibiting chirality, and confirmed an activity of the compound to stabilize the membrane protein. Therefore, the present invention has been completed based on the facts.

SUMMARY OF THE INVENTION

Therefore, the present invention is designed to solve the problems of the prior art, and it is an object of the present invention to provide a compound represented by Formula 1.

It is another object of the present invention to provide a composition for extracting, solubilizing, stabilizing, crystallizing or analyzing a membrane protein, which included the compound.

It is still another object of the present invention to provide a method of preparing the compound.

It is yet another object of the present invention to provide a method of extracting, solubilizing, stabilizing, crystallizing or analyzing a membrane protein using the compound.

According to an aspect of the present invention, there is provided a compound represented by following Formula 1:

[Formula 1]

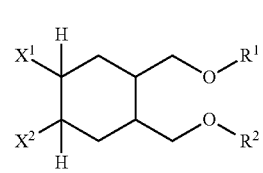

In Formula 1, $R^1$ and $R^2$ may be each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group; and $X^1$ and $X^2$ may be each independently a saccharide linked via oxygen.

The term "saccharide" used in this specification refers to a compound that is a relatively small molecule among carbohydrates and is dissolved in water to have a sweet taste. Saccharides are divided into a monosaccharide, a disaccharide, and a polysaccharide, depending on the number of molecules that constitute a sugar.

The saccharide used in the exemplary embodiment may be a monosaccharide or a disaccharide, particularly glucose or maltose, but the present invention is not limited thereto.

The saccharide may serve as a hydrophilic group. When the compound according to one exemplary embodiment of the present invention forms a complex with a membrane protein, the compound has a reduced size by linking two saccharides as hydrophilic groups in parallel to minimize an increase in the length of the hydrophilic groups while increasing the size of the hydrophilic groups. When the complex of the compound with the membrane protein has a small size, high-quality crystals of the membrane protein may be obtained (G. G. Prive, Methods 2007, 41, 388-397).

Also, $R^1$ and $R^2$ may serve as the hydrophobic groups. Two hydrophobic groups may be introduced into the compound according to one exemplary embodiment of the present invention to optimize a balance between degrees of hydrophilicity and hydrophobicity (a hydrophile-lipophile balance).

The compound according to one exemplary embodiment of the present invention may have a butane-1,2,3,4-tetraol linker exhibiting chirality. That is, the compound may have excellent performance in stabilizing and crystallizing the membrane protein since the compound is a chiral stereoisomer into which two hydrophilic groups and two hydrophobic groups are introduced using butane-1,2,3,4-tetraol having two chiral centers as a central structure.

Specifically, $R^1$ and $R^2$ may be each independently a substituted or unsubstituted $C_3$-$C_{30}$ alkyl group; $X^1$ and $X^2$ may be maltose linked via oxygen. According to one exemplary embodiment of the present invention, such a compound is named "butane-1,2,3,4-tetraol-based maltoside (BTM)."

More specifically, the compound of Formula 1 may be a compound having a stereochemical configuration represented by one of the following Formulas 1a to 1c:

[Formula 1a]

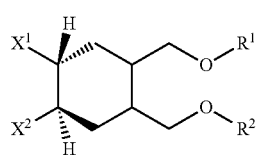

In Formula 1a, the stereochemical configuration may be represented by (2R, 3R). According to one exemplary embodiment of the present invention, the compound having such a stereochemical configuration is named "B-BTM."

[Formula 1b]

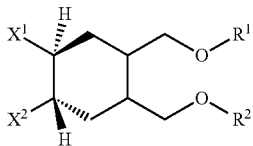

In Formula 1b, the stereochemical configuration may be represented by (2S, 3S). According to one exemplary embodiment of the present invention, the compound such a stereochemical configuration is named "A-BTM"

[Formula 1c]

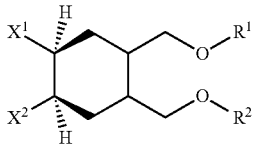

In Formula 1c, the stereochemical configuration may be represented by (2S, 3R). According to one exemplary embodiment of the present invention, the compound having such a stereochemical configuration is named "M-BTM."

According to one exemplary embodiment of the present invention, as the compound having the stereochemical configuration represented by Formula 1a, a compound in which $R^1$ and $R^2$ are each independently a $C_9$ alkyl group; and $X^1$ and $X^2$ are each independently maltose linked via oxygen is named "B-BTM-C9." Therefore, the compound may be a compound represented by the following Formula 2:

[Formula 2]

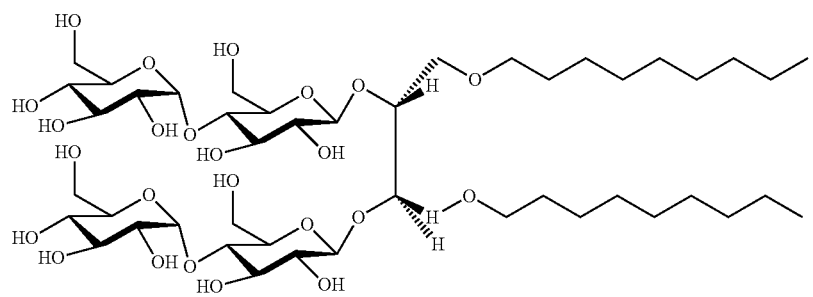

According to another exemplary embodiment of the present invention, as the compound having the stereochemical configuration represented by Formula 1a, a compound in which $R^1$ and $R^2$ are each independently a $C_{10}$ alkyl group; and $X^1$ and $X^2$ are each independently maltose linked via oxygen is named "B-BTM-C10." Therefore, the compound may be compound represented by the following Formula 3:

[Formula 3]

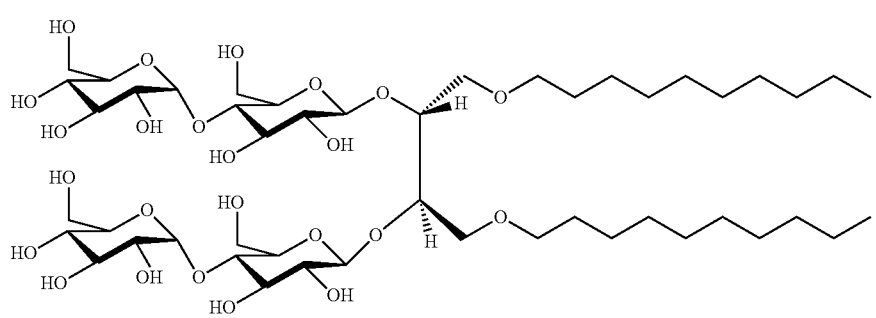

According to still another exemplary embodiment of the present invention, as the compound having the stereochemical configuration represented by Formula 1a, a compound in which $R^1$ and $R^2$ are each independently a $C_{11}$ alkyl group; and $X^1$ and $X^2$ are each independently maltose linked via oxygen is named "B-BTM-C11." Therefore, the compound may be a compound represented by the following Formula 4:

[Formula 4]

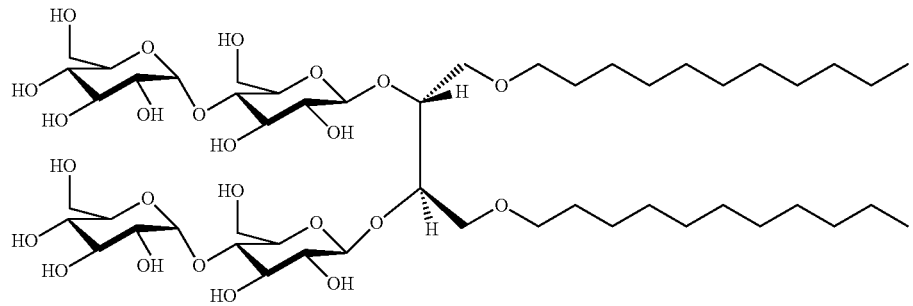

According to yet another exemplary embodiment of the present invention, as the compound having the stereochemical configuration represented by Formula 1b, a compound in which $R^1$ and $R^2$ are each independently a $C_9$ alkyl group; and $X^1$ and $X^2$ are each independently maltose linked via oxygen is named "A-BTM-C9." Therefore, the compound may be a compound represented by the following Formula 5:

[Formula 5]

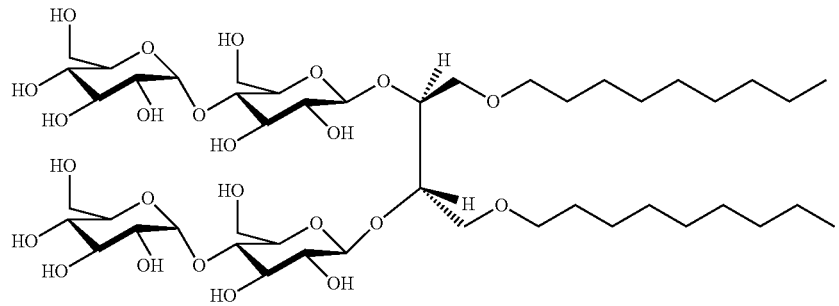

According to yet another exemplary embodiment of the present invention, as the compound having the stereochemical configuration represented by Formula 1b, a compound in which $R^1$ and $R^2$ are each independently a $C_{10}$ alkyl group; and $X^1$ and $X^2$ are each independently maltose linked via oxygen is named "A-BTM-C10." Therefore, the compound may be a compound represented by the following Formula 6:

[Formula 6]

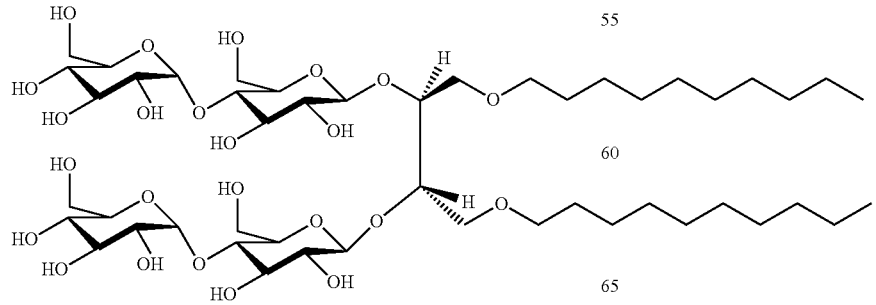

According to yet another exemplary embodiment of the present invention, as the compound having the stereochemical configuration represented by Formula 1b, a compound in which $R^1$ and $R^2$ are each independently a $C_{11}$ alkyl group; and $X^1$ and $X^2$ are each independently maltose linked via oxygen is named "A-BTM-C11." Therefore, the compound may be a compound represented by the following Formula 7:

[Formula 7]

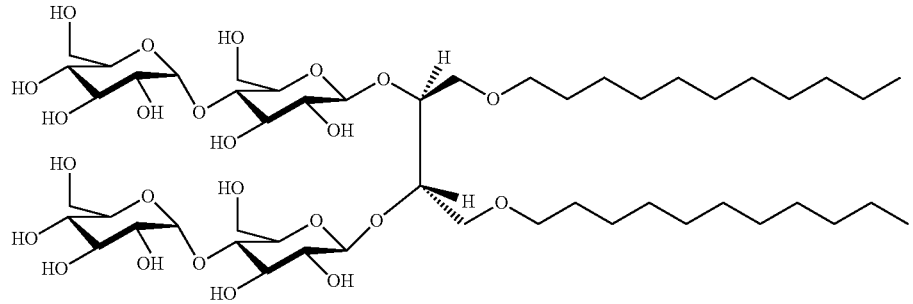

According to yet another exemplary embodiment of the present invention, as the compound having the stereochemical configuration represented by Formula 1c, a compound in which $R^1$ and $R^2$ are each independently a $C_9$ alkyl group; and $X^1$ and $X^2$ are each independently maltose linked via oxygen is named "M-BTM-C9." Therefore, the compound may be a compound represented by the following Formula 8:

[Formula 8]

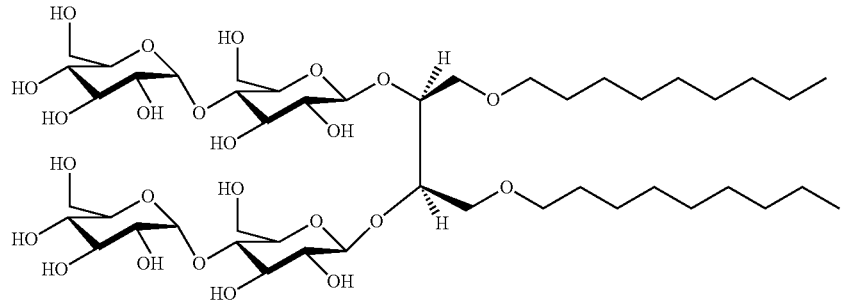

According to yet another exemplary embodiment of the present invention, as the compound having the stereochemical configuration represented by Formula 1c, a compound in which $R^1$ and $R^2$ are each independently a $C_{10}$ alkyl group; and $X^1$ and $X^2$ are each independently maltose linked via oxygen is named "M-BTM-C10." Therefore, the compound may be a compound represented by the following Formula 9:

[Formula 9]

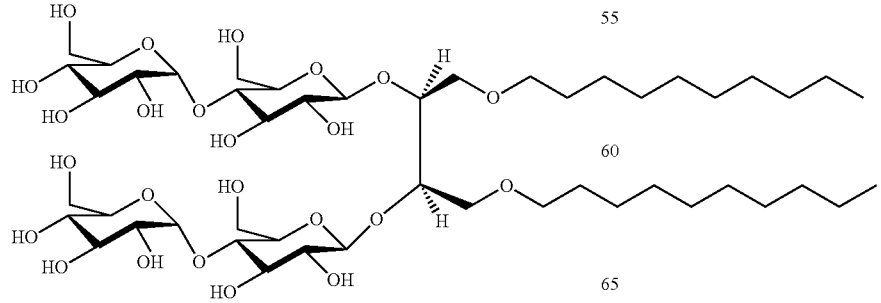

According to yet another exemplary embodiment of the present invention, as the compound having the stereochemical configuration represented by Formula 1c, a compound in which $R^1$ and $R^2$ are each independently a $C_{11}$ alkyl group; and $X^1$ and $X^2$ are each independently maltose linked via oxygen is named "M-BTM-C11." Therefore, the compound may be a compound represented by the following Formula 10:

[Formula 10]

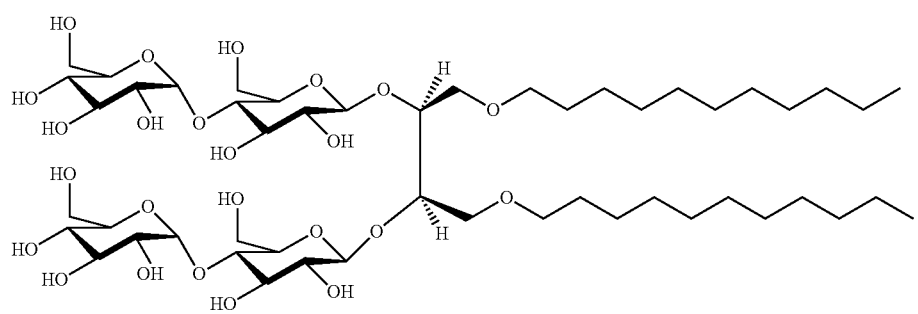

The compound according to another exemplary embodiment of the present invention may be an amphiphilic molecule for extracting, solubilizing, stabilizing, crystallizing or analyzing a membrane protein, but the present invention is not limited thereto.

Specifically, the extraction may include extracting the membrane protein from a cell membrane.

The term "amphiphilic molecule" used this specification refers to a molecule that has affinity to both polar and non-polar solvents due to the coexistence of a hydrophobic group and a hydrophilic group in one molecule. Each of the phospholipid molecules present in a surfactant or a cell membrane has a characteristic of exhibiting amphiphilicity as a molecule that has a hydrophilic group at one end thereof and a hydrophobic group at the other end thereof, thereby forming micelles or liposomes in an aqueous solution. Although the hydrophilic group exhibits polarity, the amphiphilic molecules tend not to be easily dissolved in an aqueous solution because the non-polar group co-exists in each amphiphilic molecule. However, when the concentration of the amphiphilic molecules is greater than or equal to any critical micelle concentration (CMC), round or oval micelles in which the hydrophobic groups aggregate inside and the hydrophilic groups are exposed on surfaces of the micelles may be formed due to hydrophobic interactions, resulting in significantly increased solubility in water.

A method of measuring the CMC is not particularly limited, but the CMC may be measured using methods well known in the related art. For example, the CMC may be measured by a fluorescence staining method using diphenylhexatriene (DPH).

The compound according to one exemplary embodiment of the present invention has a critical micelle concentration (CMC) of 0.0001 to 1 mM, particularly 0.0001 to 0.1 mM, more particularly 0.001 to 0.1 mM, and most particularly 0.001 to 0.05 mM in an aqueous solution, and, for example, a CMC of 0.005 to 0.05 mM in an aqueous solution, but the present invention is not limited thereto.

The BTMs according to this exemplary embodiment have a very low CMC value, compared to the DDM generally used for membrane protein research in the prior art, which has a critical micelle concentration of 0.17 mM. Therefore, since the BTMs form micelles even when present at a low concentration, a small amount of the BTMs may be used to effectively study and analyze the membrane protein. Accordingly, the BTMs may be desirable in terms of applications, compared to the DDM.

Also, according to another aspect of the present invention, there is provided a composition for extracting, solubilizing, stabilizing, crystallizing or analyzing a membrane protein, which includes the compound.

Specifically, the extraction may include extracting the membrane protein from a cell membrane.

The composition may be a micelle, liposome, emulsion or nanoparticle formulation, but the present invention is not limited thereto.

The micelles may have a radius of 2.0 nm to 20 nm, particularly 2.0 nm to 10.0 nm, more particularly 2.5 nm to 5.0 nm, and most particularly 2.7 to 5.0 nm, and, for example, a radius of 2.8 nm to 4.8 nm, but the present invention is not limited thereto.

A method of measuring the radius of the micelles is not particularly limited, but the radius of the micelles may be measured using methods well known in the related art. For example, the radius of the micelles may be measured through a dynamic light scattering (DLS) experiment.

The micelles, liposomes, emulsions or nanoparticles may bind to the membrane proteins due to internal hydrophobicity. That is, the micelles, liposomes, emulsions or nanoparticles may serve to extract the membrane proteins present in the cell membranes and enwrap the membrane proteins. Therefore, it is possible to extract the membrane proteins from the cell membranes and solubilize, stabilize, crystallize or analyze the membrane proteins using the micelles.

The composition may further include a buffer which may aid to extract, solubilize, stabilize, crystallize or analyze the membrane proteins, etc.

Also, according to still another aspect of the present invention, there is provided a method of preparing a compound represented by the following Formula 1, which includes the following steps 1) to 4):

1) performing a dialkylation reaction on (E)-but-2-ene-1, 4-diol or (Z)-but-2-ene-1,4-diol to introduce an alkyl group, particularly two alkyl groups;

2) performing a dihydroxylation reaction on the product of step 1) to synthesize a diol compound;

3) performing a glycosylation reaction on the product of step 2) to introduce a saccharide to which a protective group is attached; and 4) performing a deprotection reaction on the product of step 3):

[Formula 1]

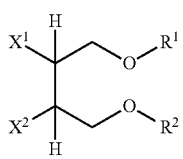

In Formula 1, $R^1$ and $R^2$ may be each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group; and $X^1$ and $X^2$ may be each independently a saccharide linked via oxygen.

Specifically, $R^1$ and $R^2$ may be each independently a substituted or unsubstituted $C_3$-$C_{30}$ alkyl group; and $X^1$ and $X^2$ may be each independently maltose linked via oxygen.

The dihydroxylation of step 2) may include Sharpless asymmetric dihydroxylation or Upjohn dihydroxylation. The "Sharpless asymmetric dihydroxylation" is a reaction in which binding in a reaction of osmium tetroxide with an alkene depends on the stereochemistry of an additive (AD-mix-t or AD-mix-13) to form a stereoselective cis vicinal diol. The "Upjohn dihydroxylation" is a reaction in which an alkene is converted into a cis vicinal diol. Since there is no reaction selectivity to two faces of the alkene, two isomers may be produced. A specific method for each of the reactions is well known in the related art.

Specifically, the compound having the stereochemical configuration represented by the following Formula 1a or 1b may be prepared by selecting the (E)-but-2-ene-1,4-diol of step 1) as a starting material and performing a Sharpless asymmetric dihydroxylation reaction in step 2):

[Formula 1a]

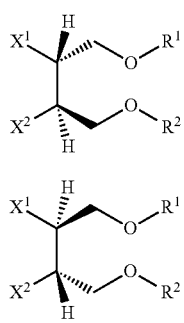

[Formula 1b]

In Formulas 1a and 1b, $R^1$, $R^2$, $X^1$, and $X^2$ have the same definitions as those defined in Formula 1.

Also, the compound having the stereochemical configuration represented by the following Formula 1c may be prepared by selecting the (Z)-but-2-ene-1,4-diol of step 1) as a starting material and performing an Upjohn dihydroxylation reaction in step 2):

[Formula 1c]

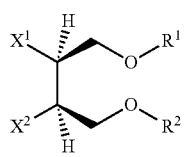

In Formula 1c, $R^1$, $R^2$, $X^1$, $X^2$ have the same definitions as those defined in Formula 1.

The compound may be a compound represented by one of Formulas 2 to 10 according to one exemplary embodiment of the present invention, but the present invention is not limited thereto.

In this exemplary embodiment, since the compound may be simply synthesized through a short 4-step synthesis process, it is possible to mass-produce the compound for membrane protein research.

According to one exemplary embodiment of the present invention, B-BTMs or A-BTMs are prepared by performing the following steps according to the synthesis scheme shown in FIG. 1:

1) adding NaH, DMF and an alkyl iodide to (E)-but-2-ene-1,4-diol and performing a dialkylation reaction to obtain a compound A.

2) adding AD-mix-t or AD-mix-13, $CH_3SO_2NH_2$, tert-BuOH and $H_2O$ to the compound A and performing a Sharpless asymmetric dihydroxylation reaction to obtain a diol compound B or C.

3) adding perbenzoylated maltosylbromide, AgOTf and DCM to the compound B or C and performing a glycosylation reaction to obtain a compound D or E into which a saccharide having a protective group attached thereto is introduced.

4) adding NaOMe and MeOH to the compound D or E and performing a deprotection (de-O-benzoylation) reaction to obtain a product F (B-BTM) or G (A-BTM).

According to another exemplary embodiment of the present invention, M-BTMs are prepared by performing the following steps according to the synthesis scheme shown in FIG. 2:

1) adding NaH, DMF and an alkyl iodide to (Z)-but-2-ene-1,4-diol and performing a dialkylation reaction to obtain a compound H.

2) adding $OsO_4$, NMO, THF and $H_2O$ to the compound H and performing an Upjohn dihydroxylation reaction to obtain a diol compound I.

3) adding perbenzoylated maltosylbromide, AgOTf and DCM to the compound I and performing a glycosylation reaction to obtain a compound J into which a saccharide having a protective group attached thereto is introduced.

4) adding NaOMe and MeOH to the compound J and performing a deprotection (de-O-benzoylation) reaction to obtain a product K (M-BTM).

According to yet another aspect of the present invention, there is provided a method of extracting, solubilizing, stabilizing, crystallizing or analyzing a membrane protein. Specifically, there is a provided a method of extracting, solubilizing, stabilizing, crystallizing or analyzing a membrane protein, which includes treating a membrane protein with the compound represented by the following Formula 1 in an aqueous solution:

[Formula 1]

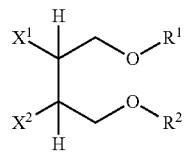

In Formula 1, $R^1$ and $R^2$ may be each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group; and $X^1$ and $X^2$ may be each independently a saccharide linked via oxygen.

Specifically, $R^1$ and $R^2$ may be each independently a substituted or unsubstituted $C_3$-$C_{30}$ alkyl group; and $X^1$ and $X^2$ may be each independently maltose linked via oxygen.

The compound may be a compound represented by one of Formulas 2 to 10 according to one exemplary embodiment of the present invention, but the present invention is not limited thereto.

Specifically, the extraction may include extracting the membrane protein from a cell membrane.

The term "membrane protein" used in this specification generally refers to a protein or glucoprotein integrated into a lipid bilayer of the cell membrane. The membrane protein is present in various states, for example, passing through the entire layer of a cell membrane or positioned on a surface of the cell membrane, or adhered on the cell membrane, etc. Examples of the membrane protein include enzymes, receptors for peptide hormones and local hormones, acceptable carriers for saccharides, ion channels, cell membrane antigens, etc., but the present invention is not limited thereto.

The membrane protein may include any proteins or glucoproteins that are integrated into the lipid bilayer of the cell membrane, and particularly a uric acid-xanthine/$H^+$ symporter (UapA), leucine transporter (LeuT), a human $\beta_2$ adrenergic receptor ($\beta_2AR$), melibiose permease (MelB), or a combination of two or more types thereof, but the present invention is not limited thereto.

The term "extraction of a membrane protein" used in this specification means that a membrane protein is separated from a cell membrane.

The term "solubilization of a membrane protein" used in this specification means that a membrane protein which is not dissolved in water is dissolved in micelles in an aqueous solution.

The term "stabilization of a membrane protein" used in this specification means that a tertiary or quaternary structure of a membrane protein is stably preserved without any change in structure and function of the membrane protein.

The term "crystallization of a membrane protein" used in this specification means that crystals of a membrane protein are formed in a solution.

The term "analysis of a membrane protein" used in this specification means that the structure or function of a membrane protein is analyzed. According to the exemplary embodiments, the analysis of the membrane protein may be performed using known methods, but the present invention is not limited thereto. For example, the structure of the membrane protein may be analyzed using electron microscopy or nuclear magnetic resonance.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the attached drawings, in which:

FIGS. 6A, 6B, 6C and 6D are diagrams showing energy-minimized structures of the BTM-C9 isomers ((A) A-BTM-C9, (B) B-BTM-C9, and (C) M-BTM-C9), and (D) a dihedral angle (X) between two hydrophobic groups and a dihedral angle (Y) between two hydrophilic groups;

Figure 9A:
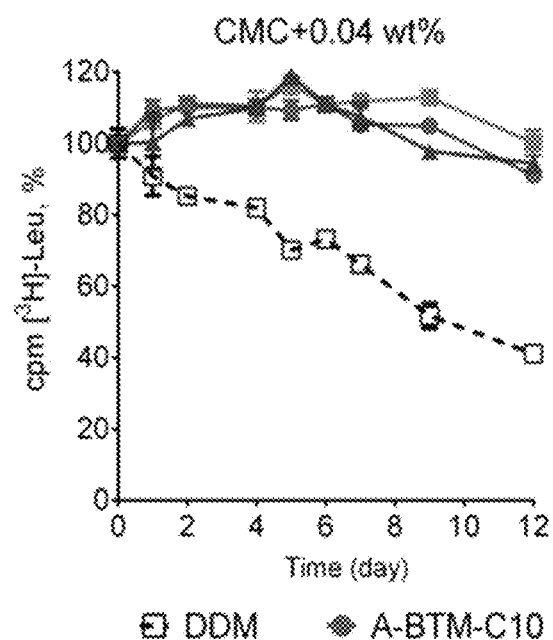
Figure 9B:
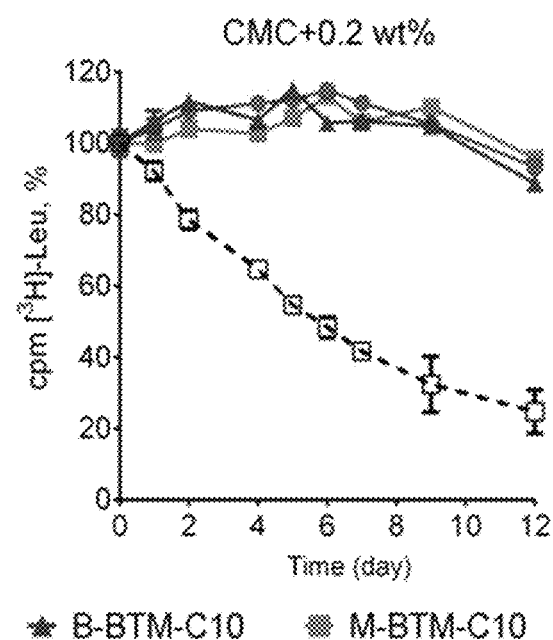
Figure 10A:
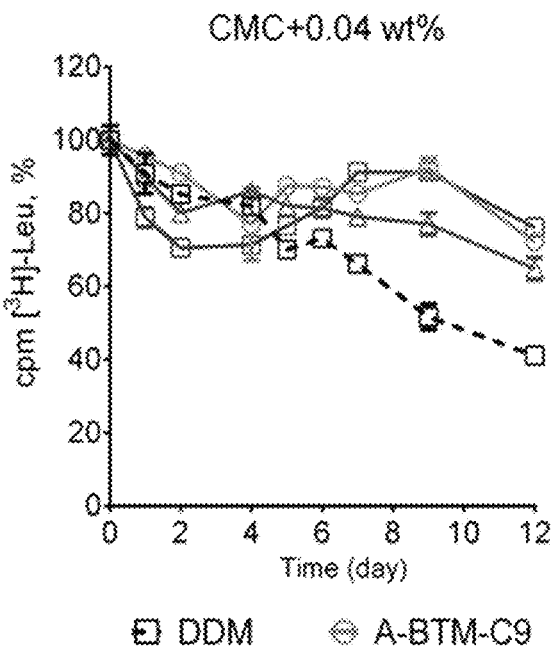
Figure 10B:
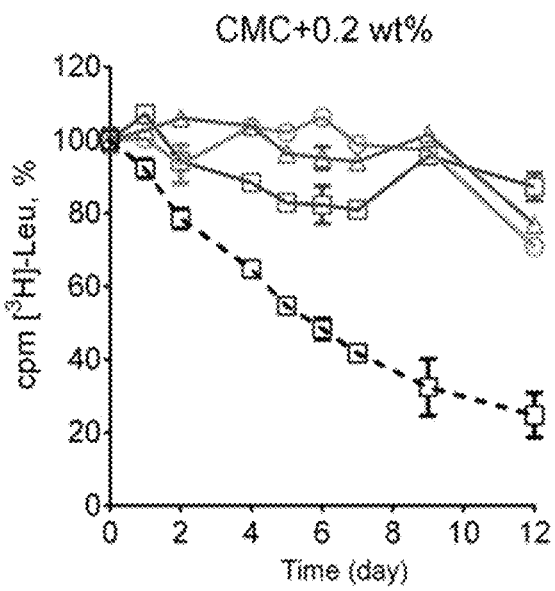
Figure 11A:
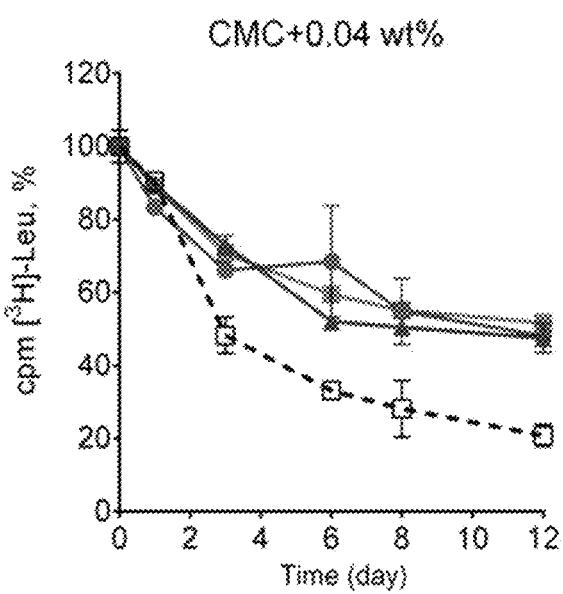
Figure 11B:
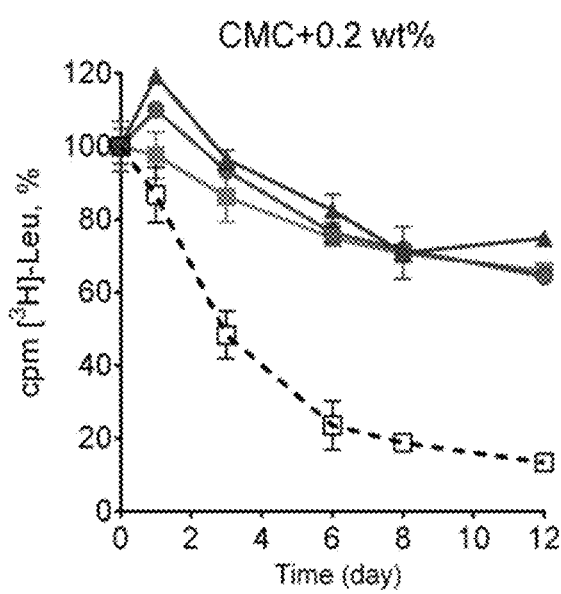
Figure 12A:
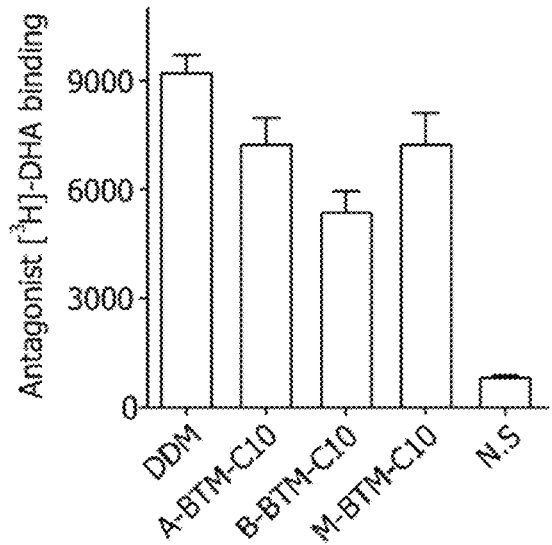
Figure 12B:
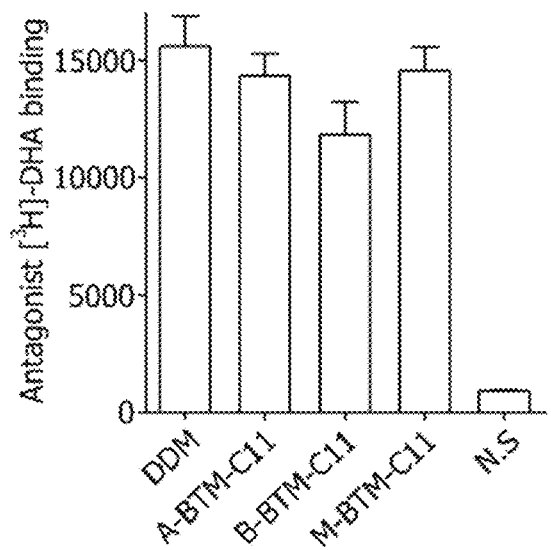
Figure 12C:
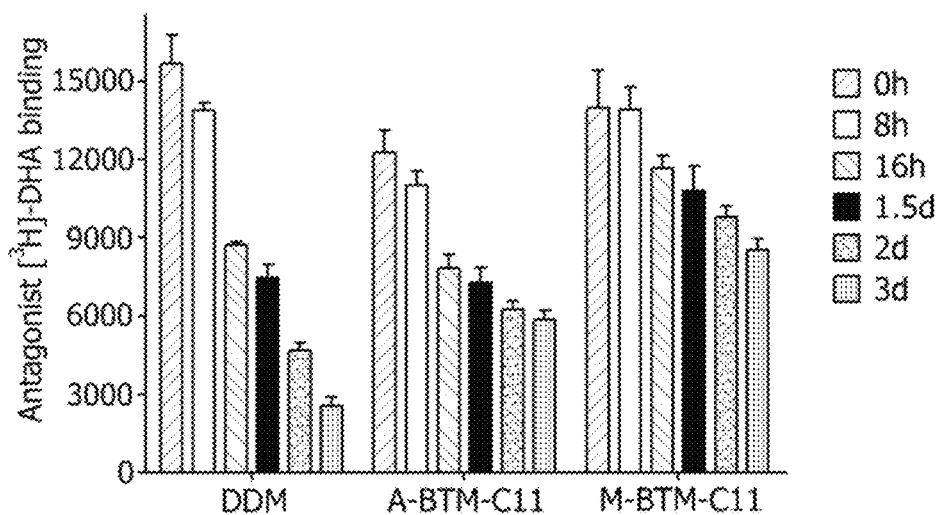
Figure 13A:
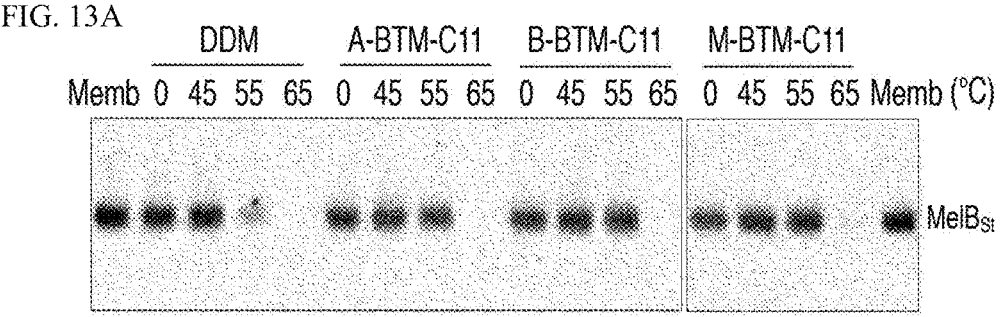
Figure 13B:
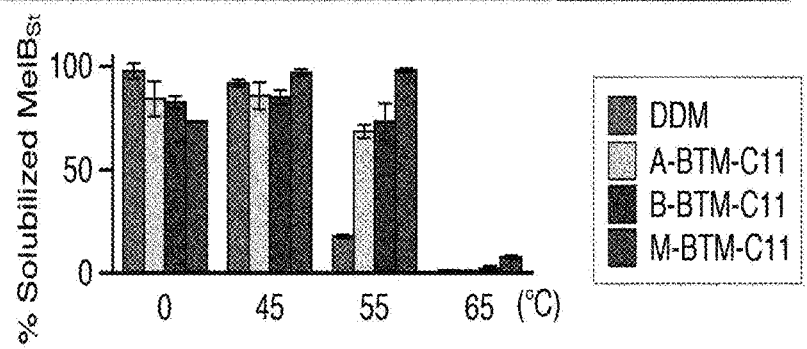

(a) BTM-C11 isomers (A-BTM-C11, B-BTM-C11, and M-BTM-C11); and (b) M-isomers having different alkyl chain lengths (M-BTM-C9, M-BTM-C10, and M-BTM-C11);

FIGS. 9A and 9B show shows results of measuring structural stability of a leucine transporter (LeuT) by BTM-C10 isomers or DDM in an aqueous solution. The protein stability was determined by measuring ligand-binding characteristics of the transporter using a scintillation proximity assay (SPA). The ligand-binding characteristics of LeuT was measured at regular intervals while the protein was incubated at room temperature for 12 days in the presence of each amphiphilic compound:

(a) BTM-C10s or DDM is present at a concentration of CMC+0.04% by weight; and (b) BTM-C10s or DDM is present at a concentration of CMC+0.2% by weight;

FIGS. 10A and 10B show shows results of measuring structural stability of the leucine transporter (LeuT) by BTM-C9 isomers or DDM in an aqueous solution. The protein stability was determined by measuring ligand-binding characteristics of the transporter using a scintillation proximity assay (SPA). The ligand-binding characteristics of LeuT was measured at regular intervals while the protein was incubated at room temperature for 12 days in the presence of each amphiphilic compound:

(a) BTM-C9s or DDM is present at a concentration of CMC+0.04% by weight; and (b) BTM-C9s or DDM is present at a concentration of CMC+0.2% by weight;

FIGS. 11A and 11B show shows results of measuring structural stability of the leucine transporter (LeuT) by BTM-C11 isomers or DDM in an aqueous solution. The protein stability was determined by measuring ligand-binding characteristics of a receptor using a scintillation proximity assay (SPA). The ligand-binding characteristics of LeuT was measured at regular intervals while the protein was incubated at room temperature for 12 days in the presence of each amphiphilic compound:

(a) BTM-C11s or DDM is present at a concentration of CMC+0.04% by weight; and (b) BTM-C11s or DDM is present at a concentration of CMC+0.2% by weight;

FIGS. 12A, 12B and 12C show shows results of measuring ligand-binding characteristics of $\beta_2AR$ by (A) BTM-C10 isomers and (B) BTM-C11 isomers. DDM is used as the control. A receptor purified with DDM is diluted with a buffer solution containing BTMs or DDM/CHS so that the final compound concentration of the receptor reaches CMC+ 0.2% by weight. The ligand-binding characteristics of the receptor were measured using a radioactive ligand [$^3$H]-DHA. Also, (C) shows results of measuring long-term stability of $\beta_2AR$ solubilized in BTM-C11 isomers or DDM/CHS. The structural stability of the receptor was measured at regular intervals while the receptor was incubated at room temperature for 3 days; and FIGS. 13A and 13B show shows results of extracting a MelB protein at four temperatures (0, 45, 55, and 65° C.) using a BTM-C11 isomer (A-BTM-C11, B-BTM-C11 or M-BTM-C11) or DDM at a concentration of 1.5% by weight, incubating the MelB protein at the same temperature for 90 minutes and measuring an amount of the MelB protein dissolved in an aqueous solution:

(A) SDS-PAGE and Western Blotting results showing amounts of the MelB protein extracted using the respective amphiphilic compounds; and (B) a histogram showing the amounts of the MelB protein extracted using the respective amphiphilic compounds as a percentage of the total amount of proteins present in a membrane sample (Memb) which is not treated with the amphiphilic compounds.

DESCRIPTION OF SPECIFIC EMBODIMENTS OF THE INVENTION

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms "first," "second," etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

<Example 1> Synthesis Method of BTMs

Figure 1:
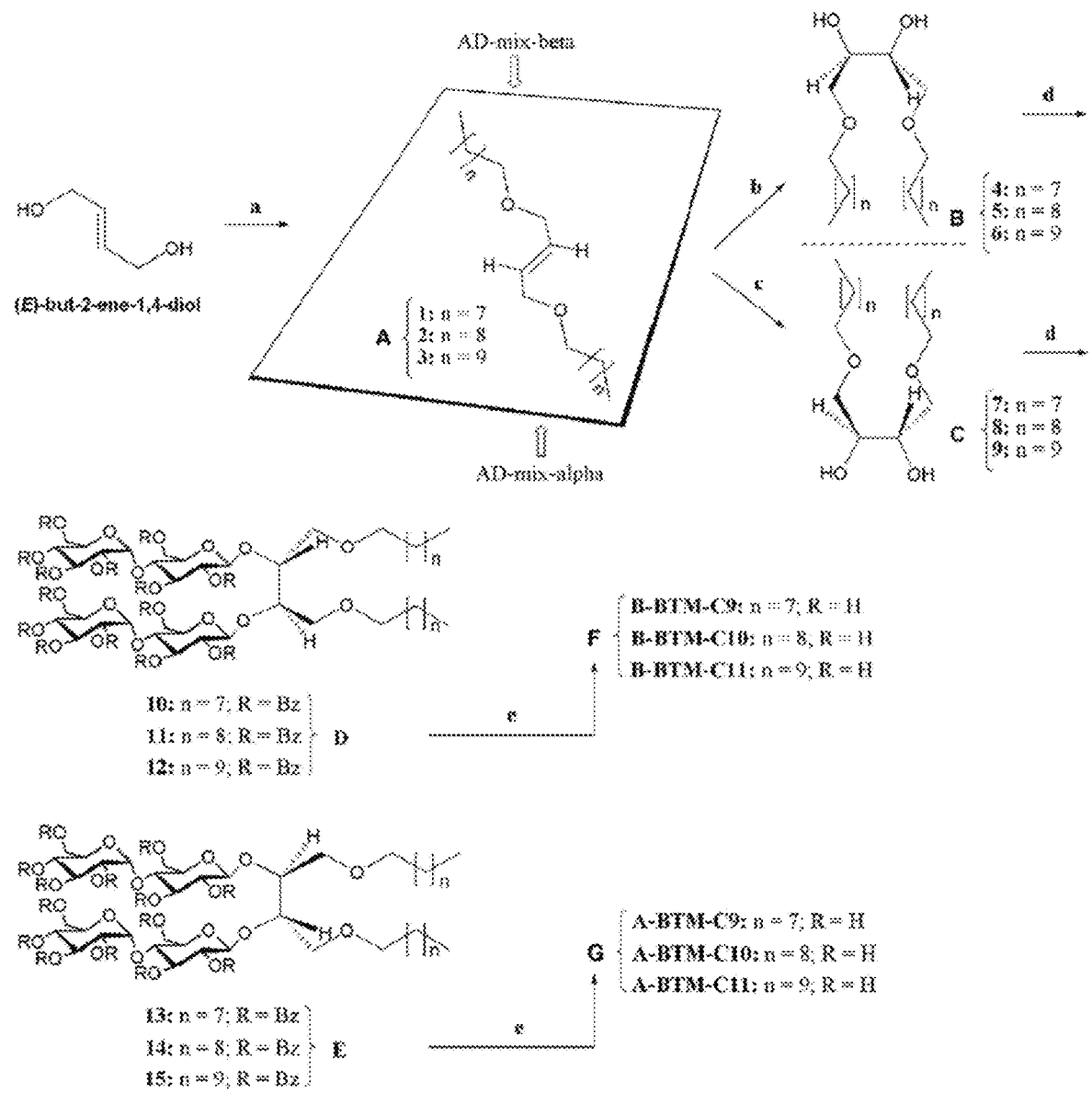
FIG. 1 is a diagram showing a synthesis scheme of B-BTMs and A-BTMs according to Example 1 of the present invention.
Figure 2:
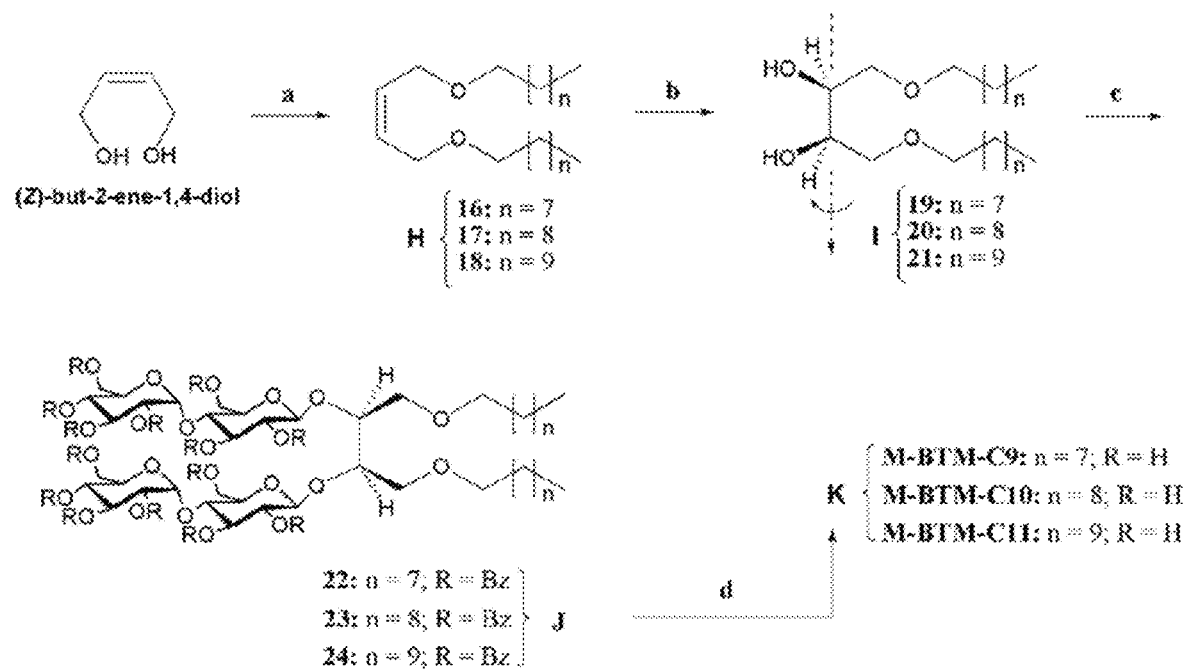
FIG. 2 is a diagram showing a synthesis scheme of M-BTMs according to Example 1 of the present invention.
Figure 3:
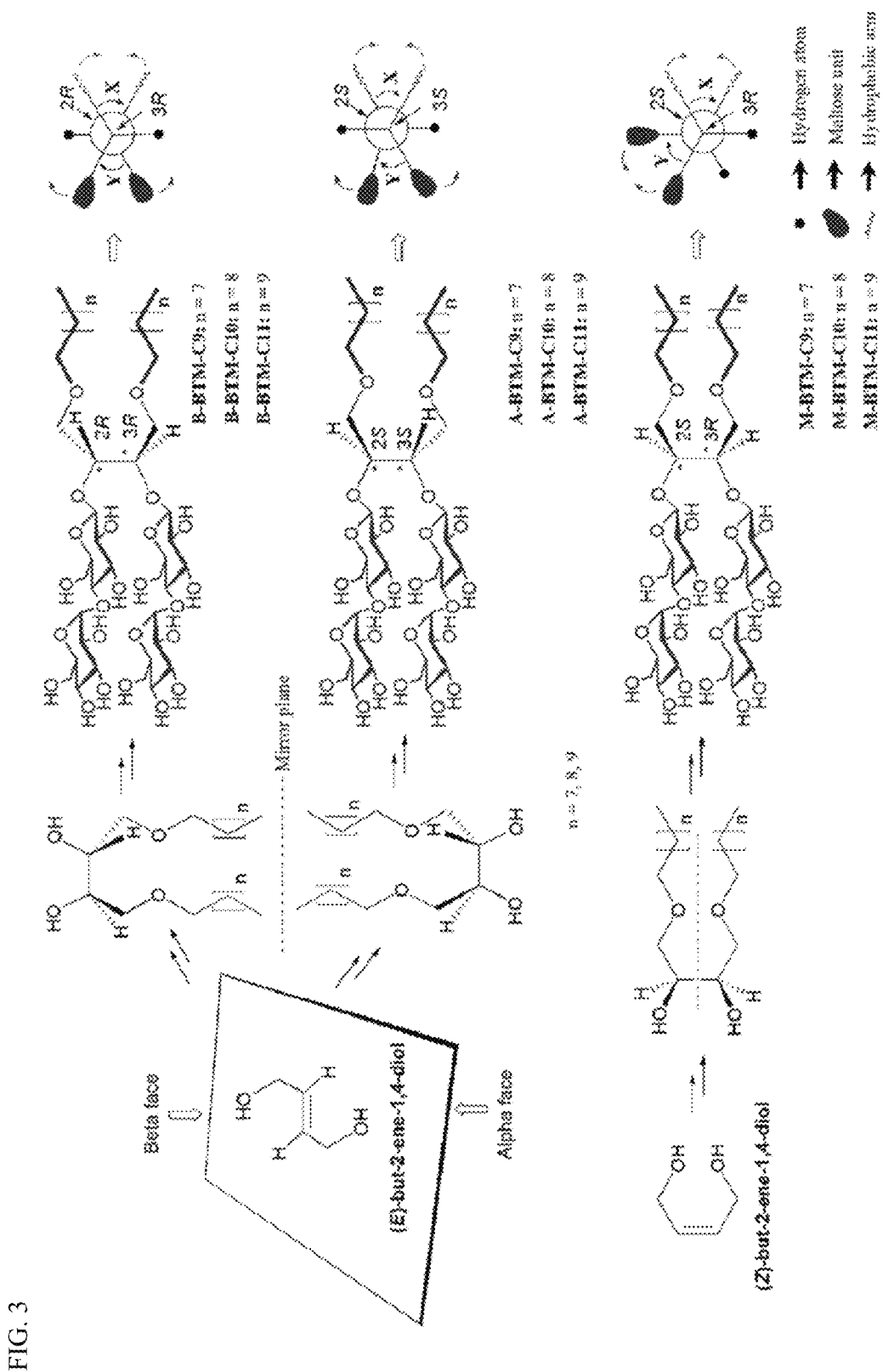
FIG. 3 is a diagram showing chemical structures of BTMs according to examples of the present invention. Each of the Newman projections for respective isomers has a dihedral angle (X) between two hydrophobic groups and a dihedral angle (Y) between two hydrophilic groups.

Synthesis schemes of BTMs are shown in FIGS. 1 and 2. As three types of a butane-1,2,3,4-tetraol-based maltoside (BTM) stereoisomer, A-BTM ($\alpha$-BTM), B-BTM ($\beta$-BTM) and M-BTM (meso-BTM) were synthesized according to the following synthesis methods of Examples <1-1> to <1-4>, each of which was performed in triplicate to synthesize a total of 9 compounds. The compounds are shown in FIG. 3.

<1-1> Typical Synthesis Procedure for Dialkylation (Step a in FIG. 1 and FIG. 2)

(E)-but-2-ene-1,4-diol or (Z)-but-2-ene-1,4-diol (1 equiv.: 500 mg), and NaH (3.0 equiv.) were dissolved in DMF (15 mL) at 0° C. An alkyl iodide (2.9 equiv.) was slowly added thereto, and the resulting solution was stirred at 80° C. for 3 days. When the reaction was completed (the completion of the reaction was confirmed through thin layer chromatography (TLC), the solution was diluted with diethyl ether (150 mL), and sequentially washed with a 1 M HCl aqueous solution (2×20 mL) and brine (100 mL). An organic layer was dried with anhydrous Na$_2$SO$_4$, and the solvent was removed using a rotary evaporator. The residue was purified by silica gel column chromatography (EtOAc/hexane) to obtain a compound A or H in a liquid state.

<1-2> Typical Synthesis Procedure for Sharpless Asymmetric Dihydroxylation (Steps b and c in FIG. 1)

5 mL of tert-butyl alcohol, 5 mL of water, and 1.4 g of AD-mix-$\beta$ or AD-mix-$\alpha$ were put into a 25 mL round-bottom flask equipped with a magnetic stirrer. The resulting mixture was stirred at room temperature to form two layers; a lower aqueous solution layer had a pale yellow color. Then, methanesulfonamide (95 mg; 1 equiv. based on 1 mmol of olefin) was added. The resulting mixture was cooled to 0° C., and some of the dissolved salts were precipitated accordingly. 1 mmol of trans-olefin A was immediately added, and a heterogeneous slurry was stirred at 0° C. for 48 hours (this procedure was monitored by TLC). Solid sodium sulfite (1.5 g) was added while the mixture was stirred at 0° C., and the mixture was warmed at room temperature, and then stirred for 30 to 60 minutes. Ethyl acetate (10 mL) was added to the reaction mixture to separate layers. Then, an aqueous solution layer was further extracted with an organic solvent (3×15 mL). The organic layer was washed with 2 N KOH. The organic extract was dried with anhydrous sodium sulfate, and concentrated to obtain a diol and a ligand. The resulting crude products were purified by flash chromatography (silica gel, EtOAc/hexane; the ligand was immobilized in this solvent system) to obtain optically active 1,2-diol (compound B or C) with a yield of 90 to 95%.

<1-2'> Typical synthesis procedure for Upjohn dihydroxylation (Step b in FIG. 2)

An NMO (1.5 equiv.) solution (50% by weight) dissolved in water was added to a mixture of THF and water (15 mL of a 9:1 mixture) at 0° C. The compound H (500 mg, 1 equiv.) was added, and the resulting mixture was stirred for 15 minutes, and OsO$_4$ (2.5% by weight of a solution dissolved in tBuOH: 1.4 mL) was then slowly added for 20 minutes or more using a syringe. The mixture was stirred at room temperature for 12 hours. The reaction was stopped by addition of sodium sulfite (8 g), and the reaction solution was diluted with water (30 mL). The solution was extracted with EtOAc (2×70 mL). The organic extract was dried ($Na_2SO_4$), and concentrated in a vacuum, and the residues were purified by silica gel column chromatography (EtOAc/hexane) to obtain meso 1,2-diol (compound I) as orange gum.

<1-3> Typical Synthesis Procedure for Glycosylation Reaction (Step d in FIG. 1 and Step c in FIG. 2)

This was based on the synthesis method by P. R. Ashton, et al. (*Chem. Eur. J.* 1996, 2, 1115-1128.). Specifically, a mixture in which the compound B, C or I (1 equiv., 250 mg), AgOTf (2.4 equiv.), and 2,4,6-collidine (1.0 equiv.) were dissolved in anhydrous $CH_2Cl_2$ (40 mL) was stirred at −45° C. A perbenzoylated maltosylbromide (2.4 equiv.) solution (10 mL) dissolved in $CH_2Cl_2$ was slowly added to the resulting solution for 30 minutes or more. The solution was continuously stirred at −45° C. for 30 minutes, and the reaction mixture was slowly warmed to 0° C., and stirred for an hour. When the reaction was completed, pyridine was added to the reaction mixture, and the mixture was diluted with $CH_2Cl_2$ (40 mL), and then filtered through Celite. The filtrate was sequentially washed with a 1 M $Na_2S_2O_3$ (40 mL) aqueous solution, a 0.1 M HCl aqueous solution (40 mL), and brine (2×40 mL). The organic layer was dried with anhydrous $Na_2SO_4$, and the solvent was removed using a rotary evaporator. The residue was purified by silica gel column chromatography (EtOAc/hexane) to obtain a glycosylated compound (compound D, E or J) in a glossy white solid state.

<1-4> Typical Synthesis Procedure for Deprotection Reaction (Step e in FIG. 1 and Step d in FIG. 2)

In this procedure, de-O-benzoylation or de-O-acetylation was performed under Zemplen's conditions according to the synthesis method by P. R. Ashton, et al. (*Chem. Eur. J.* 1996, 2, 1115-1128.). Specifically, the O-protected compound D, E or J was dissolved in MeOH, and NaOMe, which was a 0.5 M methanolic solution, was added thereto so that the final concentration of NaOMe reached 0.05 M. The reaction mixture was stirred at room temperature for 14 hours, and then neutralized with an Amberlite IR-120 ($H^+$ form) resin. The resin was removed through filtration, the reaction mixture was washed with MeOH, and the solvent was then in vacuo removed from the filtrate. The residue was purely purified by silica gel column chromatography (MeOH/$CH_2Cl_2$). The residue was recrystallized with $CH_2Cl_2$/MeOH/diethyl ether to obtain a further purified white solid compound F, G or K. The compound F thus obtained was the compound B-BTM according to the present invention, the compound G was the compound A-BTM according to the present invention, and the compound K was the compound M-BTM according to the present invention.

<Preparative Example 1> Synthesis of B-BTM-C9

<1-1> Synthesis of Compound 1

A compound 1 was synthesized with a yield of 85% according to the typical synthesis procedure for dialkylation as described in Example 1-1. $^1$H NMR (400 MHz, $CDCl_3$): δ 5.81-5.80 (m, 2H), 3.97 (dd, J=3.2 Hz, 1.6 Hz, 4H), 3.41 (t, J=6.8 Hz, 4H), 1.59-1.56 (m, 4H), 1.40-1.27 (m, 24H), 0.88 (t, J=6.8 Hz, 6H); $^{13}$C NMR (100 MHz, $CDCl_3$): δ 129.7, 71.0, 70.8, 32.1, 30.0, 29.8, 29.7, 29.5, 26.4, 22.9, 14.3.

<1-2> Synthesis of Compound 4

A compound 4 was synthesized with a yield of 94% according to the typical synthesis procedure for Sharpless asymmetric dihydroxylation using AD-mix-β as described in Example 1-2. $^1$H NMR (400 MHz, $CDCl_3$): δ 3.85-3.80 (m, 2H), 3.58-3.54 (m, 4H), 3.49-3.45 (m, 4H), 2.92 (d, J=4.8 Hz, 2H), 1.58 (app. t, J=7.2 Hz, 4H), 1.39-1.20 (m, 24H), 0.88 (t, J=6.4 Hz, 6H); $^{13}$C NMR (100 MHz, $CDCl_3$): δ 73.0, 72.1, 70.9, 32.1, 29.8 (2C), 29.7, 29.5, 26.3, 22.9, 14.3; $[\alpha]_D^{20}$=−2.871 degcm$^3$ g$^{-1}$ dm$^{-1}$ (c=1.22 gcm$^{-3}$ in acetone).

<1-3> Synthesis of Compound 10

A compound 10 was synthesized with a yield of 85% according to the typical procedure for a glycosylation reaction as described in Example 1-3. $^1$H NMR (400 MHz, $CDCl_3$): δ 8.21-7.77 (m, 26H), 7.67-7.65 (m, 6H), 7.53-7.20 (m, 42H), 6.17 (t, J=9.6 Hz, 2H), 5.79-5.70 (m, 6H), 5.31 (d, J=8 Hz, 2H), 5.24 (t, J=6.8 Hz, 2H), 5.04 (d, J=12 Hz, 2H), 4.93 (d, J=8 Hz, 2H), 4.67 (d, J=8 Hz, 2H), 4.57-4.50 (m, 4H), 4.43-4.33 (m, 4H), 3.99 (d, J=4 Hz, 2H), 3.87 (d, J=8 Hz, 2H), 3.45 (d, J=10 Hz, 2H), 3.20 (t, J=8 Hz, 2H), 2.94-2.85 (m, 4H), 1.29-1.07 (m, 24H), 1.00-0.92 (m, 4H), 0.88 (t, J=4 Hz, 6H); $^{13}$C NMR (100 MHz, $CDCl_3$): δ 166.2, 166.0, 165.8, 165.6, 165.2, 165.1, 133.9, 133.5, 133.3, 133.2, 132.9, 130.1 (2C), 129.9 (2C), 129.8, 129.7 (2C), 129.5, 129.1, 129.0 (2C), 128.9, 128.7, 128.5, 128.3, 128.2 (2C), 100.8, 96.6, 79.7, 75.1, 73.6, 72.7, 72.5, 71.5, 71.1, 70.3, 70.1, 69.3, 63.4, 63.6, 62.7, 32.0, 29.7, 29.6 (2C), 29.4, 26.0, 22.8, 14.3.

<1-4> Synthesis of B-BTM-C9

Figure 4A:
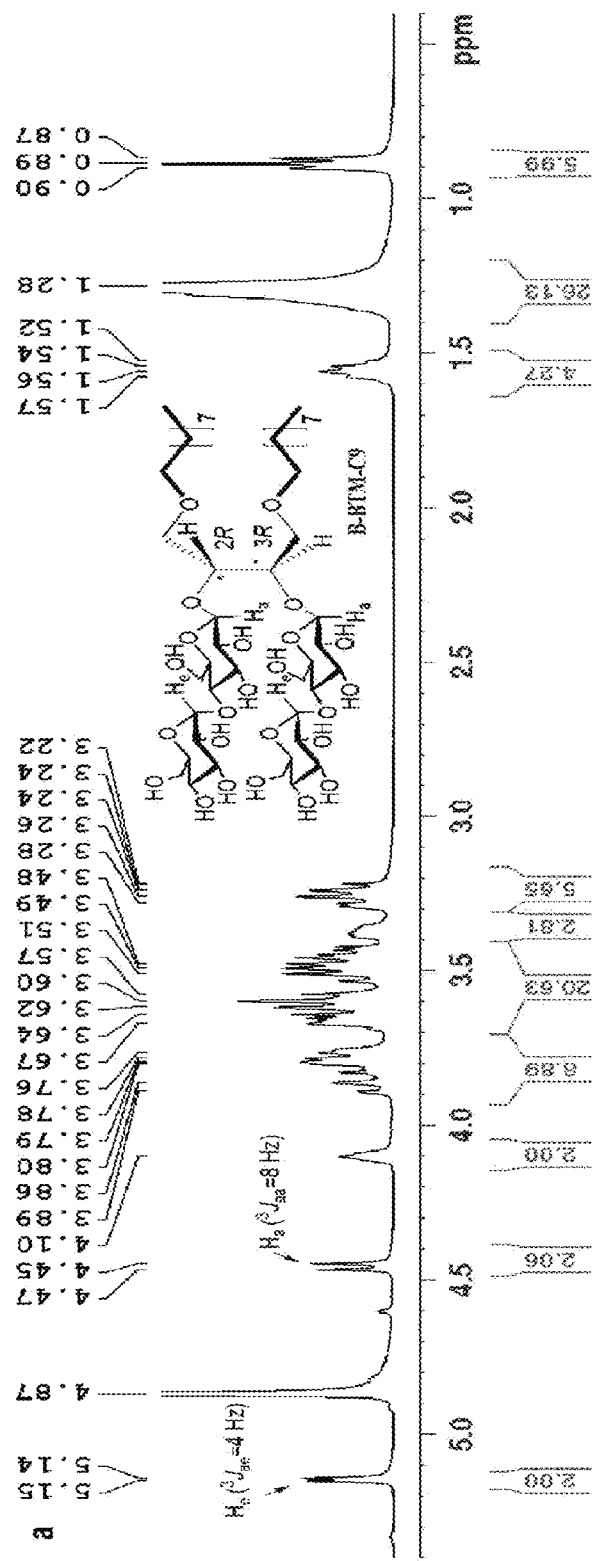
FIG. 4A is a diagram showing the $^1H$ NMR spectrum of B-BTM-C9 as a BTM-C9 isomer.

B-BTM-C9 was synthesized with a yield of 94% according to the typical synthesis procedure for a deprotection reaction as described in Example 1-4. The $^1$H NMR spectrum is shown in FIG. 4A. $^1$H NMR (400 MHz, $CD_3OD$): δ 5.15 (d, J=4 Hz, 2H), 4.46 (d, J=8 Hz, 2H), 4.10 (br s, 2H), 3.80-3.67 (m, 9H), 3.55-3.15 (m, 28H), 1.48-1.45 (m, 4H), 1.28-1.14 (m, 28H), 0.89 (t, J=6.4 Hz, 6H); $^{13}$C NMR (100 MHz, $CD_3OD$): δ 104.6, 103.0, 81.4, 79.2, 77.7, 76.8, 75.1, 74.9 (2C), 74.2, 72.7, 71.5, 71.2, 62.8, 62.5, 62.3, 33.2, 30.9 (2C), 30.8, 30.6, 27.4, 23.9, 14.6; HRMS (EI): calcd. for $C_{46}H_{86}O_{24}Na^+[M+Na]^+$ 1045.5407, found 1045.5411.

<Preparative Example 2> Synthesis of B-BTM-C10

<2-1> Synthesis of Compound 2

A compound 2 was synthesized with a yield of 80% according to the typical synthesis procedure for dialkylation as described in Example 1-1. $^1$H NMR (400 MHz, $CDCl_3$): δ 5.81-5.79 (m, 2H), 3.97 (dd, J=4 Hz, 1.6 Hz, 4H), 3.41 (t, J=8 Hz, 4H), 1.60-1.55 (m, 4H), 1.38-1.26 (m, 28H), 0.88 (t, J=8 Hz, 6H); $^{13}$C NMR (100 MHz, $CDCl_3$): δ 129.7, 71.0, 70.7, 32.1, 30.0, 29.8 (2C), 29.7, 29.5, 26.4, 22.9, 14.3.

<2-2> Synthesis of Compound 5

A compound 5 was synthesized with a yield of 95% according to the typical synthesis procedure for Sharpless asymmetric dihydroxylation using AD-mix-β as described in Example 1-2. $^1$H NMR (400 MHz, $CDCl_3$): δ 3.85-3.80 (m, 2H), 3.59-3.54 (m, 4H), 3.49-3.45 (m, 4H), 3.08 (d, J=4 Hz, 2H), 1.58 (app. t, J=8 Hz, 4H), 1.38-1.22 (m, 28H), 0.88 (t, J=8 Hz, 6H); $^{13}$C NMR (100 MHz, $CDCl_3$): δ 72.8, 72.0, 70.7, 32.0, 29.7 (2C), 29.6, 29.5, 26.2, 22.8, 14.2; $[\alpha]_D^{20}$=−3.301 degcm$^3$ g$^{-1}$ dm$^{-1}$ (c=1.11 gcm$^3$ in acetone).

<2-3> Synthesis of Compound 11

A compound 11 was synthesized with a yield of 88% according to the typical procedure for a glycosylation reaction as described in Example 1-3. $^1$H NMR (400 MHz, $CDCl_3$): δ 8.20-7.77 (m, 25H), 7.67-7.65 (m, 6H), 7.55-7.17 (m, 44H), 6.17 (t, J=10 Hz, 2H), 5.77-5.71 (m, 6H), 5.33 (d, J=8 Hz, 2H), 5.24 (t, J=6.8 Hz, 2H), 5.06 (d, J=10 Hz, 2H), 4.68 (d, J=4 Hz, 2H), 4.67 (d, J=8 Hz, 2H), 4.53-4.50 (m, 4H), 4.43-4.36 (m, 4H), 3.99 (d, J=6 Hz, 2H), 3.89 (d, J=8 Hz, 2H), 3.45 (d, J=10 Hz, 2H), 3.20 (t, J=4 Hz, 2H), 2.92-2.85 (m, 4H), 1.25-1.07 (m, 32H), 0.98-0.90 (m, 4H), 0.88 (t, J=4 Hz, 6H); $^{13}$C NMR (100 MHz, CDCl$_3$): δ 166.1, 166.0, 165.7, 165.6, 165.1 (2C), 133.9, 133.6, 133.3, 133.1, 132.9, 130.1 (2C), 129.9 (2C), 129.8 (2C), 129.7 (2C), 129.5, 129.1, 129.0 (2C), 128.8, 128.7, 128.6, 125.5 (2C), 128.3, 128.2 (2C), 100.8, 96.6, 79.7, 75.1, 73.6 (2C), 72.7, 72.5, 71.5, 71.0, 70.3, 70.1, 69.3, 63.4, 63.6, 62.6, 32.1, 29.7 (2C), 29.6 (2C), 29.5, 26.0, 22.8, 14.3.

<2-4> Synthesis of B-BTM-C10

B-BTM-C10 was synthesized with a yield of 92% according to the typical synthesis procedure for a deprotection reaction as described in Example 1-4. $^1$H NMR (400 MHz, CD$_3$OD): δ 5.15 (d, J=4 Hz, 2H), 4.46 (d, J=8 Hz, 2H), 4.11 (br s, 2H), 3.91-3.81 (m, 9H), 3.68-3.24 (m, 27H), 1.61-1.54 (m, 4H), 1.38-1.23 (m, 30H), 0.90 (t, J=6.8 Hz, 6H); $^{13}$C NMR (100 MHz, CD$_3$OD): δ 104.6, 102.9, 81.3, 79.1, 77.7, 76.7, 75.1, 74.8 (2C), 74.1, 72.6, 71.4, 71.1, 62.7, 62.5, 33.2, 30.9, 30.8, 30.7, 30.6, 27.4, 23.8, 14.7; HRMS (EI): calcd. for C$_{48}$H$_{90}$O$_{24}$Na$^+$ [M+Na]$^+$ 1073.5720, found 1073.5718.

<Preparative Example 3> Synthesis of B-BTM-C11

<3-1> Synthesis of Compound 3

A compound 3 was synthesized with a yield of 79% according to the typical synthesis procedure for dialkylation as described in Example 1-1. $^1$H NMR (400 MHz, CDCl$_3$): δ 5.82-5.80 (m, 2H), 3.97 (dd, J=4 Hz, 1.6 Hz, 4H), 3.41 (t, J=8 Hz, 4H), 1.61-1.54 (m, 4H), 1.40-1.26 (m, 34H), 0.88 (t, J=8 Hz, 6H); $^{13}$C NMR (100 MHz, CDCl$_3$): δ 129.7, 71.0, 70.8, 32.1, 30.0, 29.8 (2C), 29.7, 29.6, 26.4, 22.9, 14.3.

<3-2> Synthesis of Compound 6

A compound 6 was synthesized with a yield of 90% according to the typical synthesis procedure for Sharpless asymmetric dihydroxylation using AD-mix-13 as described in Example 1-2. $^1$H NMR (400 MHz, CDCl$_3$): δ 3.85-3.81 (m, 2H), 3.55-3.51 (m, 4H), 3.46-3.43 (m, 4H), 2.98 (d, J=4 Hz, 2H), 1.56 (app. t, J=8 Hz, 4H), 1.36-1.24 (m, 32H), 0.86 (t, J=8 Hz, 6H); $^{13}$C NMR (100 MHz, CDCl$_3$): δ 72.9, 72.0, 70.8, 32.1, 29.8 (2C), 29.7, 29.5, 26.3, 22.9, 14.3; [α]$_D^{20}$=−3.654 degcm$^3$ g$^{-1}$ dm$^{-1}$ (c=0.60 gcm$^3$ in acetone).

<3-3> Synthesis of Compound 12

A compound 12 was synthesized with a yield of 84% according to the typical synthesis procedure for a glycosylation reaction as described in Example 1-3. $^1$H NMR (400 MHz, CDCl$_3$): δ 8.19-7.70 (m, 24H), 7.67-7.65 (m, 6H), 7.55-7.19 (m, 43H), 6.17 (t, J=8 Hz, 2H), 5.79-5.70 (m, 6H), 5.32 (d, J=8 Hz, 2H), 5.23 (t, J=6.8 Hz, 2H), 5.03 (d, J=12 Hz, 2H), 4.94 (d, J=4 Hz, 2H), 4.56 (d, J=8 Hz, 2H), 4.57-4.50 (m, 4H), 4.43-4.35 (m, 4H), 3.99 (d, J=8 Hz, 2H), 3.87 (d, J=8 Hz, 2H), 3.45 (d, J=10 Hz, 2H), 3.21 (t, J=4 Hz, 2H), 2.93-2.85 (m, 4H), 1.26-1.13 (m, 34H), 1.00-0.92 (m, 4H), 0.87 (t, J=4 Hz, 6H); $^{13}$C NMR (100 MHz, CDCl$_3$): δ 166.2, 166.1, 165.7 (2C), 165.6, 165.2, 165.1, 133.8, 133.6 (2C), 133.3, 133.2, 132.8, 130.1 (2C), 129.9 (2C), 129.8 (2C), 129.7, 129.5, 129.1, 129.0 (2C), 128.9, 128.7 (2C), 128.5, 128.3, 128.2 (2C), 100.8, 96.6, 79.7, 75.1, 73.6, 72.7, 72.5, 71.5, 71.0, 70.3, 70.1, 69.3, 63.4, 63.6, 62.7, 32.1, 29.8 (2C), 29.7, 29.6, 29.5, 29.4, 26.0, 22.9, 14.3.

<3-4> Synthesis of B-BTM-C11

B-BTM-C11 was synthesized with a yield of 95% according to the typical synthesis procedure for a deprotection reaction as described in Example 1-4. $^1$H NMR (400 MHz, CD$_3$OD): δ 5.16 (d, J=4 Hz, 2H), 4.46 (d, J=8 Hz, 2H), 4.10 (br s, 2H), 3.90-3.79 (m, 8H), 3.68-3.22 (m, 26H), 1.59-1.54 (m, 4H), 1.38-1.23 (m, 32H), 0.90 (t, J=8 Hz, 6H); $^{13}$C NMR (100 MHz, CD$_3$OD): δ 104.6, 103.0, 81.5, 79.2, 77.8, 76.8, 75.2, 74.9 (2C), 74.2, 72.7, 71.5, 71.2, 62.8, 62.6, 33.2, 30.8, 30.7, 27.5, 23.9, 14.6; HRMS (EI): calcd. for C$_{50}$H$_{94}$O$_{24}$Na$^+$ [M+Na]$^+$ 1101.6033, found 1101.6035.

<Preparative Example 4> Synthesis of A-BTM-C9

<4-1> Synthesis of Compound 1

A compound was synthesized with a yield of 85% according to the typical synthesis procedure for dialkylation as described in Example 1-1. $^1$H NMR (400 MHz, CDCl$_3$): δ 5.81-5.80 (m, 2H), 3.97 (dd, J=3.2 Hz, 1.6 Hz, 4H), 3.41 (t, J=6.8 Hz, 4H), 1.59-1.56 (m, 4H), 1.40-1.27 (m, 24H), 0.88 (t, J=6.8 Hz, 6H); $^{13}$C NMR (100 MHz, CDCl$_3$): δ 129.7, 71.0, 70.8, 32.1, 30.0, 29.8, 29.7, 29.5, 26.4, 22.9, 14.3.

<4-2> Synthesis of Compound 7

A compound 7 was synthesized with a yield of 90% according to the typical synthesis procedure for Sharpless asymmetric dihydroxylation using AD-mix-α as described in Example 1-2. The compound 7 had the same $^1$H and $^{13}$C NMR as the compound 4, indicating that the compounds 4 and 7 are enantiomers of each other. [α]$_D^{20}$=+2.874 degcm$^3$ g$^1$ dm$^{-1}$ (c=1.24 gcm$^{-3}$ in acetone).

<4-3> Synthesis of Compound 13

A compound 13 was synthesized with a yield of 83% according to the typical procedure for a glycosylation reaction as described in Example 1-3. $^1$H NMR (400 MHz, CDCl$_3$): δ 8.19-7.73 (m, 26H), 7.70-7.59 (m, 6H), 7.58-7.18 (m, 4H), 6.10 (t, J=8 1 Hz, 2H), 5.72-5.67 (m, 6H), 5.31 (t, J=8 Hz, 2H), 5.20 (d, J=6.8 Hz, 2H), 4.71 (d, J=8 Hz, 2H), 4.57-4.54 (m, 4H), 4.44-4.33 (m, 6H), 4.29-4.24 (m, 2H), 3.76 (br s, 2H), 3.41-3.32 (m, 4H), 3.17-3.10 (m, 5H), 1.33-1.14 (m, 27H), 0.88 (t, J=8 Hz, 6H); $^{13}$C NMR (100 MHz, CDCl$_3$): δ 166.2, 166.1, 165.9, 165.8, 165.7, 165.2 (2C), 165.1, 133.7, 133.6 (2C), 133.5 (2C), 133.3, 133.1 (2C), 130.0 (2C), 129.9 (2C), 129.7, 129.6, 129.5, 129.4, 129.3, 129.0, 128.8 (2C), 128.7, 128.5, 128.2, 100.7, 96.5, 79.0, 75.0, 73.1, 73.0, 72.2, 71.8, 71.4, 70.5, 69.9, 69.2 (2C), 63.3, 62.6, 32.1, 29.8, 29.7 (2C), 29.6, 29.5, 26.2, 22.9, 14.3.

<4-4> Synthesis of A-BTM-C9

Figure 4B:
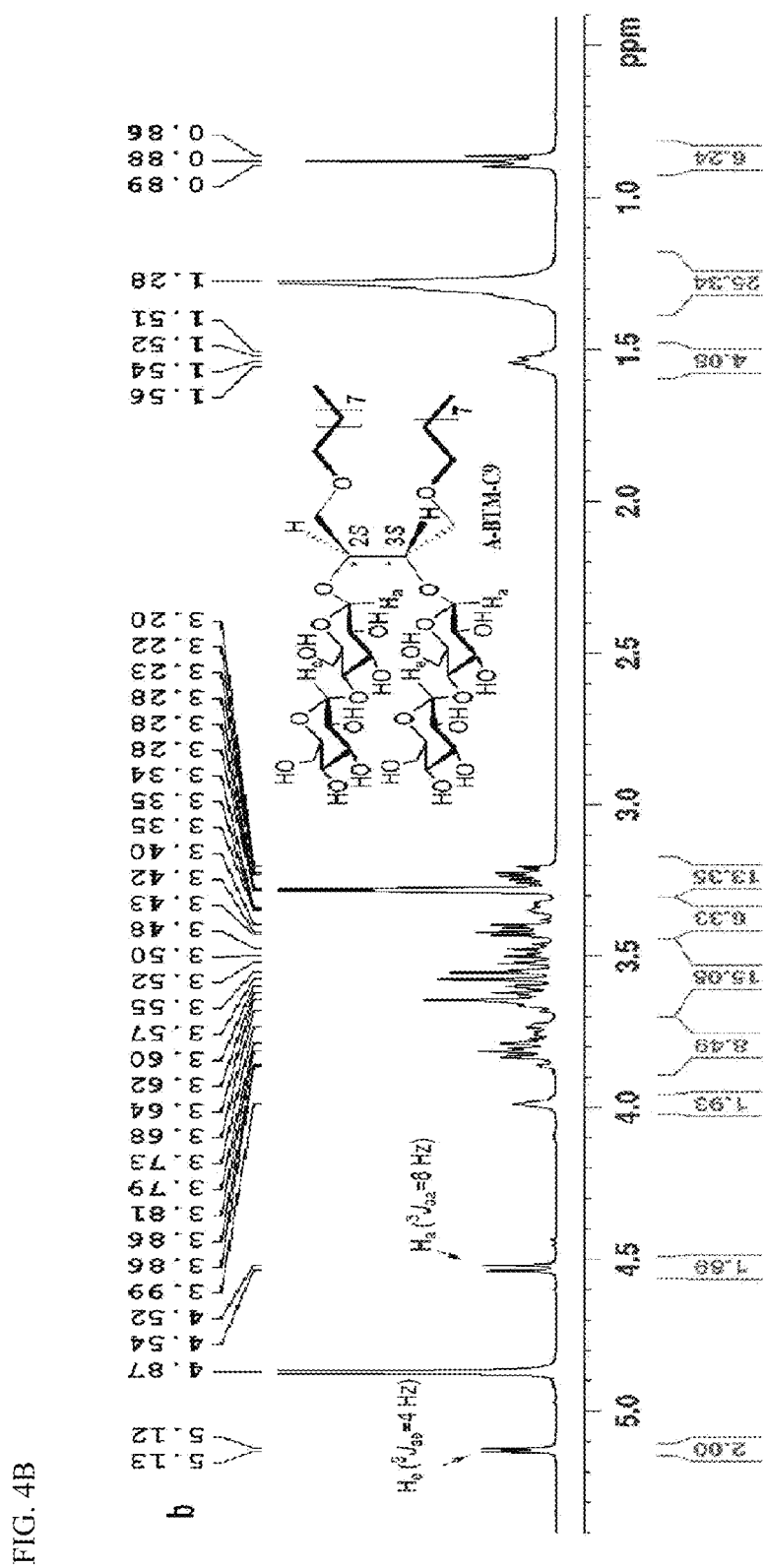
FIG. 4B is a diagram showing the $^1H$ NMR spectrum of A-BTM-C9 as a BTM-C9 isomer.

A-BTM-C9 was synthesized with a yield of 92% according to the typical synthesis procedure for a deprotection reaction as described in Example 1-4. The $^1$H NMR spectrum is shown in FIG. 4B. $^1$H NMR (400 MHz, CD$_3$OD): δ 5.13 (d, J=4 Hz, 2H), 4.53 (d, J=8 Hz, 2H), 4.02 (br s, 2H), 3.86-3.59 (m, 21H), 3.50-3.25 (m, 14H), 1.58-1.55 (m, 4H), 1.30 (br s, 24H), 0.88 (t, J=6.4 Hz, 6H); $^{13}$C NMR (100 MHz, CD$_3$OD): δ 105.3, 103.1, 81.3, 79.9, 78.0, 76.8, 75.2, 75.1, 74.9, 74.3, 72.7, 71.6, 62.9, 62.3, 33.2, 30.9 (2C), 30.8, 30.6, 27.6, 23.9, 14.6; HRMS (EI): calcd. for C$_{46}$H$_{86}$O$_{24}$Na$^+$ [M+Na]$^+$ 1045.5407, found 1045.5410.

<Preparative Example 5> Synthesis of A-BTM-C10

<5-1> Synthesis of Compound 2

A compound 2 was synthesized with a yield of 80% according to the typical synthesis procedure for dialkylation as described in Example 1-1. $^1$H NMR (400 MHz, CDCl$_3$): δ 5.81-5.79 (m, 2H), 3.97 (dd, J=4 Hz, 1.6 Hz, 4H), 3.41 (t, J=8 Hz, 4H), 1.60-1.55 (m, 4H), 1.38-1.26 (m, 28H), 0.88 (t, J=8 Hz, 6H); $^{13}$C NMR (100 MHz, CDCl$_3$): δ 129.7, 71.0, 70.74, 32.1, 30.0, 29.8 (2C), 29.7, 29.5, 26.4, 22.9, 14.3.

<5-2> Synthesis of Compound 8

A compound 8 was synthesized with a yield of 94% according to the typical synthesis procedure for Sharpless asymmetric dihydroxylation using AD-mix-α as described in Example 1-2. The compound 8 had the same $^1$H and $^{13}$C NMR as the compound 5, indicating that the compounds 5 and 8 are enantiomers of each other. $[\alpha]_D^{20}$=+3.311 degcm$^3$ g$^1$ dm$^{-1}$ (c=1.19 gcm$^{-3}$ in acetone).

<5-3> Synthesis of Compound 14

A compound 14 was synthesized with a yield of 82% according to the typical procedure for a glycosylation reaction as described in Example 1-3. $^1$H NMR (400 MHz, CDCl$_3$): δ 8.07-7.72 (m, 24H), 7.70-7.59 (m, 6H), 7.58-7.18 (m, 42H), 6.12 (t, J=10 Hz, 2H), 5.70-5.66 (m, 6H), 5.30 (t, J=8 Hz, 2H), 5.22 (d, J=8 Hz, 2H), 4.72 (d, J=10 Hz, 2H), 4.57-4.56 (m, 4H), 4.40-4.30 (m, 6H), 4.29-4.24 (m, 2H), 3.79 (br s, 2H), 3.44-3.32 (m, 4H), 3.20-3.09 (m, 5H), 1.34-1.16 (m, 35H), 0.88 (t, J=6.8 Hz, 6H); $^{13}$C NMR (100 MHz, CDCl$_3$): δ 166.1, 166.0, 165.9, 165.7, 165.2 (2C), 165.0, 133.7, 133.6, 133.5 (2C), 133.3, 133.2, 130.0 (2C), 129.9 (2C), 129.7, 129.6, 129.5, 129.4, 129.1, 129.0, 128.8 (2C), 128.7, 128.5, 128.3, 100.6, 96.4, 79.0, 75.0, 73.1, 73.0, 72.2, 71.8, 71.4, 70.5, 69.9, 69.2 (2C), 63.3, 62.6, 32.1, 29.8 (3C), 29.7, 29.6, 29.5, 26.2, 22.9, 14.3.

<5-4> Synthesis of A-BTM-C10

A-BTM-C10 was synthesized with a yield of 91% according to the typical synthesis procedure for a deprotection reaction as described in Example 1-4. $^1$H NMR (400 MHz, CD$_3$OD): δ 5.08 (d, J=3.6 Hz, 2H), 4.47 (d, J=8 Hz, 2H), 3.91 (br s, 2H), 3.76-3.34 (m, 29H), 3.20-3.15 (m, 4H), 1.49-1.45 (m, 4H), 1.20 (br s, 28H), 0.81 (t, J=6.8 Hz, 6H); $^{13}$C NMR (100 MHz, CD$_3$OD): δ 105.2, 103.0, 81.2, 80.0, 78.0, 77.9, 76.7, 75.2, 75.1, 74.8, 74.2, 72.6, 71.6, 71.5, 62.8, 62.3, 33.2, 30.9 (2C), 30.8 (2C), 30.6, 27.5, 27.4, 23.9, 14.6; HRMS (EI): calcd. for C$_{48}$H$_{90}$O$_{24}$Na$^+$ [M+Na]$^+$ 1073.5720, found 1073.5718.

<Preparative Example 6> Synthesis of A-BTM-C11

<6-1> Synthesis of Compound 3

A compound 3 was synthesized with a yield of 79% according to the typical synthesis procedure for dialkylation as described in Example 1-1. $^1$H NMR (400 MHz, CDCl$_3$): δ 5.82-5.80 (m, 2H), 3.97 (dd, J=4 Hz, 1.6 Hz, 4H), 3.41 (t, J=8 Hz, 4H), 1.61-1.54 (m, 4H), 1.40-1.26 (m, 34H), 0.88 (t, J=8 Hz, 6H); $^{13}$C NMR (100 MHz, CDCl$_3$): δ 129.7, 71.0, 70.8, 32.1, 30.0, 29.8 (2C), 29.7, 29.6, 26.4, 22.9, 14.3.

<6-2> Synthesis of Compound 9

A compound 9 was synthesized with a yield of 95% according to the typical synthesis procedure for Sharpless asymmetric dihydroxylation using AD-mix-α as described in Example 1-2. The compound 9 had the same $^1$H and $^{13}$C NMR as the compound 6, indicating that the compounds 6 and 8 are enantiomers of each other. $[\alpha]_D^{20}$=+3.652 degcm$^3$ g$^1$ dm$^{-1}$ (c=0.75 gcm$^{-3}$ in acetone).

<6-3> Synthesis of Compound 15

A compound 15 was synthesized with a yield of 87% according to the typical procedure for a glycosylation reaction as described in Example 1-3. $^1$H NMR (400 MHz, CDCl$_3$): δ 8.17-7.70 (m, 26H), 7.68-7.55 (m, 6H), 7.58-7.16 (m, 44H), 6.13 (t, J=8 Hz, 2H), 5.72-5.67 (m, 6H), 5.32 (t, J=8 Hz, 2H), 5.27 (d, J=6.8 Hz, 2H), 4.79 (d, J=8 Hz, 2H), 4.57-4.54 (m, 4H), 4.40-4.30 (m, 6H), 4.28-4.24 (m, 2H), 3.88 (br s, 2H), 3.44-3.32 (m, 4H), 3.21-3.09 (m, 5H), 1.33-1.14 (m, 38H), 0.94 (app. t, J=4 Hz, 6H); $^{13}$C NMR (100 MHz, CDCl$_3$): δ 166.1, 166.0, 165.9, 165.7, 165.2 (2C), 165.1, 133.7, 133.6, 133.5 (2C), 133.3, 133.1 (2C), 130.0 (2C), 129.9 (2C), 129.8 (2C), 129.6, 129.5, 129.4, 129.1 (2C), 128.8 (2C), 128.7, 128.5, 128.3, 100.6, 96.4, 79.0, 75.0, 73.1, 73.0, 72.1, 71.7, 71.3, 70.5, 69.9, 69.1, 62.6, 60.4, 32.0, 29.8, 29.7, 29.6 (3C), 29.5, 26.1, 22.8, 21.1, 14.2

<6-4> Synthesis of A-BTM-C11

A-BTM-C11 was synthesized with a yield of 95% according to the typical synthesis procedure for a deprotection reaction as described in Example 1-4. $^1$H NMR (400 MHz, CD$_3$OD): δ 5.17 (app. s, 2H), 4.57 (d, J=8 Hz, 2H), 4.01 (br s, 2H), 3.86-3.43 (m, 34H), 3.31-3.27 (m, 6H), 1.58-1.55 (m, 4H), 1.29 (br s, 34H), 0.90 (t, J=8 Hz, 6H); $^{13}$C NMR (100 MHz, CD$_3$OD): δ 105.2, 103.0, 81.2, 80.0, 77.9, 76.7, 75.1 (2C), 74.8, 74.2, 72.6, 71.6, 71.5, 62.8, 62.3, 33.2, 31.0, 30.9 (2C), 30.8 (2C), 30.6, 27.5, 23.9, 14.6; HRMS (EI): calcd. for C$_{50}$H$_{94}$O$_{24}$Na$^+$ [M+Na]$^+$ 1101.6033, found 1101.6036.

<Preparative Example 7> Synthesis of M-BTM-C9

<7-1> Synthesis of Compound 16

A compound 16 was synthesized with a yield of 82% according to the typical synthesis procedure for dialkylation as described in Example 1-1. $^1$H NMR (400 MHz, CDCl$_3$): δ 5.71-5.70 (m, 2H), 4.04 (d, J=4.8 Hz, 4H), 3.41 (t, J=6.8 Hz, 4H), 1.61-1.54 (m, 4H), 1.39-1.27 (m, 24H), 0.88 (t, J=6.8 Hz, 6H); $^{13}$C NMR (100 MHz, CDCl$_3$): δ 129.7, 70.8, 66.6, 32.1, 30.0, 29.8, 29.7, 29.5, 26.4, 22.9, 14.3.

<7-2> Synthesis of Compound 19

A compound 19 was synthesized with a yield of 91% according to the typical synthesis procedure for Upjohn dihydroxylation as described in Example 1-2'. $^1$H NMR (400 MHz, CDCl$_3$): δ 3.77 (br s, 2H), 3.62-3.55 (m, 4H), 3.47 (t, J=8 Hz, 4H), 2.90 (d, J=4 Hz, 2H), 1.61-1.52 (m, 4H), 1.48-1.22 (m, 24H), 0.88 (t, J=8 Hz, 6H); $^{13}$C NMR (100 MHz, CDCl$_3$): δ 72.2, 71.8, 71.2, 32.0, 29.7 (2C), 29.6, 29.4, 26.2, 22.8, 14.2.

<7-3> Synthesis of Compound 22

A compound 22 was synthesized with a yield of 82% according to the typical procedure for a glycosylation reaction as described in Example 1-3. $^1$H NMR (400 MHz, CDCl$_3$): δ 8.11-7.67 (m, 27H), 7.62-7.19 (m, 42H), 6.97 (t, J=8 Hz, 1H), 6.91 (t, J=8 Hz, 1H), 6.19-6.09 (m, 2H), 5.91-5.67 (m, 4H), 5.32-5.21 (m, 4H), 5.00-4.70 (m, 5H), 4.55-4.32 (m, 5H), 4.30-4.19 (m, 4H), 4.03 (br s, 2H), 3.44-3.19 (m, 4H), 2.93 (app. t, J=4 Hz, 1H), 2.46 (t, J=6.8 Hz, 2H), 1.40-1.00 (m, 22H), 0.92-0.85 (m, 6H); $^{13}$C NMR (100 MHz, CDCl$_3$): δ 166.0, 165.8, 165.7 (2C), 165.6, 165.3, 165.2, 165.1 (2C), 164.9, 133.7, 133.6, 133.5, 133.4, 133.3 (2C), 133.2 (2C), 133.0, 132.8, 130.4, 130.2, 130.0 (4C), 129.9 (2C), 129.8, 129.7, 129.6 (2C), 129.2 (2C), 129.1 (2C), 129.0, 128.9 (2C), 128.8, 128.7 (2C), 128.6, 128.5 (2C), 128.4, 128.3, 128.2 (2C), 128.1, 100.7, 99.4, 96.6, 95.8, 78.8, 75.6, 74.8, 73.6, 72.8 (2C), 72.7, 72.4, 71.6, 71.4, 71.1, 70.6, 70.3, 70.2, 70.1, 69.2, 69.1, 63.7, 63.6, 62.7, 32.1, 29.8, 29.7 (2C), 29.6, 29.5 (2C), 29.4, 26.1, 25.9, 22.9 (2C), 14.3 (2C).

<7-4> Synthesis of M-BTM-C9

Figure 4C:
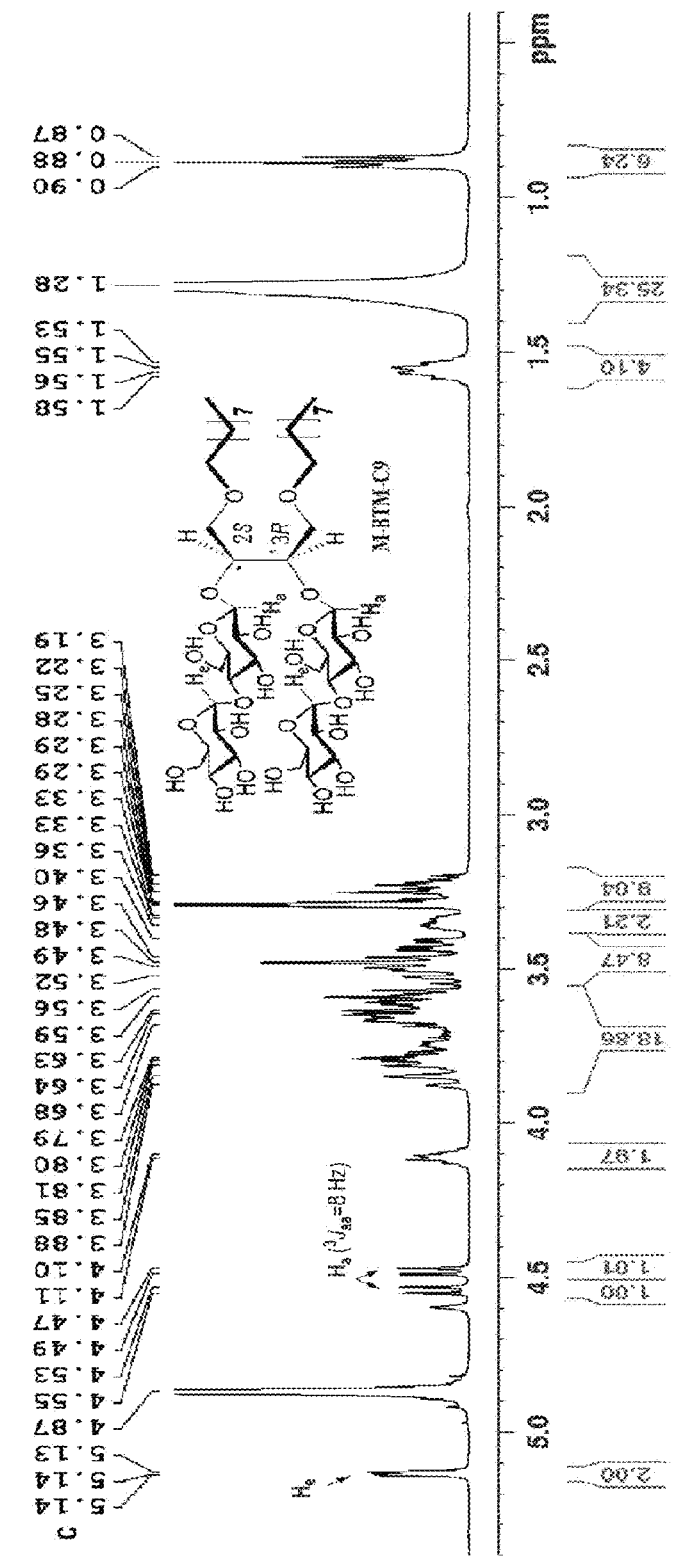
FIG. 4C is a diagram showing the $^1H$ NMR spectrum of M-BTM-C9 as a BTM-C9 isomer.

M-BTM-C9 was synthesized with a yield of 94% according to the typical synthesis procedure for a deprotection reaction as described in Example 1-4. The $^1$H NMR spectrum is shown in FIG. 4C. $^1$H NMR (400 MHz, CD$_3$OD): δ 5.14-5.13 (dd, J=3.6, 1.2 Hz, 2H), 4.54 (d, J=8.0 Hz, 1H), 4.48 (d, J=8.0 Hz, 1H), 4.16-4.10 (m, 2H), 3.89-3.43 (m, 27H), 3.40-3.33 (m, 2H), 3.31-3.21 (m, 9H), 1.61-1.52 (m, 4H), 1.40-1.26 (m, 25H), 0.88 (t, J=6.4 Hz, 6H); $^{13}$C NMR (100 MHz, CD$_3$OD): δ 104.4, 104.2, 103.0, 81.3, 79.6, 79.5, 77.8, 77.7, 76.7, 75.1 (2C), 75.0, 74.9, 74.2, 72.7, 72.6, 71.7, 71.5, 71.1, 62.8, 62.4, 62.3, 33.2, 30.9 (3C), 30.8 (2C), 30.6, 27.5 (2C), 23.9, 14.7; HRMS (EI): calcd. for $C_{46}H_{86}O_{24}Na^+$ $[M+Na]^+$ 1045.5407, found 1045.5411.

<Preparative Example 8> Synthesis of M-BTM-C10

<8-1> Synthesis of Compound 17

A compound 17 was synthesized with a yield of 78% according to the typical synthesis procedure for dialkylation as described in Example 1-1. $^1$H NMR (400 MHz, CDCl$_3$): δ 5.72-5.69 (m, 2H), 4.03 (d, J=4 Hz, 4H), 3.40 (t, J=8 Hz, 4H), 1.60-1.53 (m, 4H), 1.39-1.25 (m, 28H), 0.87 (t, J=8 Hz, 6H); $^{13}$C NMR (100 MHz, CDCl$_3$): δ 129.7, 70.8, 66.7, 32.1, 30.0, 29.8 (2C), 29.7, 29.5, 26.4, 22.9, 14.3.

<8-2> Synthesis of Compound 20

A compound 20 was synthesized with a yield of 90% according to the typical synthesis procedure for Upjohn dihydroxylation as described in Example 1-2'. $^1$H NMR (400 MHz, CDCl$_3$): δ 3.78 (br s, 2H), 3.62-3.56 (m, 4H), 3.47 (t, J=8 Hz, 4H), 2.86 (d, J=4 Hz, 2H), 1.62-1.53 (m, 4H), 1.40-1.26 (m, 28H), 0.88 (t, J=8 Hz, 6H); $^{13}$C NMR (100 MHz, CDCl$_3$): δ 72.2, 72.0, 71.3, 32.1, 29.8 (2C), 29.7, 29.5, 26.3, 22.9, 14.3.

<8-3> Synthesis of Compound 23

A compound 23 was synthesized with a yield of 84% according to the typical procedure for a glycosylation reaction as described in Example 1-3. $^1$H NMR (400 MHz, CDCl$_3$): δ 8.15-7.62 (m, 27H), 7.60-7.12 (m, 41H), 6.08 (t, J=8 Hz, 1H), 6.90 (t, J=8 Hz, 1H), 6.19-6.12 (m, 2H), 5.45-5.62 (m, 4H), 5.36-5.20 (m, 4H), 5.02-4.71 (m, 5H), 4.52-4.35 (m, 5H), 4.32-4.19 (m, 4H), 4.05 (br s, 2H), 3.49-3.25 (m, 4H), 2.95 (app. t, J=4 Hz, 1H), 2.47 (t, J=4 Hz, 2H), 1.43-1.08 (m, 26H), 0.96-0.86 (m, 6H); $^{13}$C NMR (100 MHz, CDCl$_3$): δ 166.2, 165.8, 165.7 (2C), 165.6, 165.5, 165.3, 165.1 (2C), 164.9, 133.8, 133.6, 133.5, 133.4, 133.3 (2C), 133.2 (2C), 133.1, 132.7, 130.4, 130.2, 130.0 (3C), 129.9 (3C), 129.8, 129.7, 129.6 (2C), 129.2 (3C), 129.1, 129.0, 128.9 (2C), 128.8, 128.7 (2C), 128.6, 128.5 (2C), 128.4, 128.3, 128.2 (2C), 128.1, 100.7, 99.4, 96.6, 95.8, 78.8, 75.6, 74.8, 73.6, 72.8 (2C), 72.7, 72.4, 71.5, 71.4, 71.1, 70.7, 70.3, 70.2, 70.0, 69.2, 69.0, 63.7, 63.6, 62.6, 32.1 (2C), 29.7 (2C), 29.6, 29.5, 29.4, 26.1, 25.9, 22.9, 22.8, 14.3 (2C).

<8-4> Synthesis of M-BTM-C10

M-BTM-C10 was synthesized with a yield of 95% according to the typical synthesis procedure for a deprotection reaction as described in Example 1-4. $^1$H NMR (400 MHz, CD$_3$OD): δ 5.16 (br s, 2H), 4.56 (d, J=8 Hz, 1H), 4.50 (d, J=8 Hz, 1H), 4.14-4.11 (m, 2H), 3.89-3.46 (m, 30H), 3.38-3.37 (m, 2H), 3.30-3.25 (m, 6H), 1.62-1.53 (m, 4H), 1.40-1.24 (m, 30H), 0.90 (t, J=8 Hz, 6H); $^{13}$C NMR (100 MHz, CD$_3$OD): δ 104.4, 104.2, 103.1, 103.0, 81.4, 81.3, 79.6, 79.5, 77.8, 77.7, 76.7, 75.1 (2C), 75.0, 74.9, 74.2, 72.7, 72.6, 71.7, 71.5, 71.1, 62.8, 62.4, 62.3, 33.2, 31.0 (2C), 30.9 (2C), 30.8 (2C), 30.7, 30.6, 27.5 (2C), 23.9, 14.7; HRMS (EI): calcd. for $C_{48}H_{90}O_{24}Na^+$ $[M+Na]^+$ 1073.5720, found 1073.5723.

<Preparative Example 9> Synthesis of M-BTM-C11

<9-1> Synthesis of Compound 18

A compound 18 was synthesized with a yield of 84% according to the typical synthesis procedure for dialkylation as described in Example 1-1. $^1$H NMR (400 MHz, CDCl$_3$): δ 5.72-5.70 (m, 2H), 4.04 (d, J=4 Hz, 4H), 3.41 (t, J=8 Hz, 4H), 1.57-1.53 (m, 4H), 1.39-1.26 (m, 34H), 0.88 (t, J=8 Hz, 6H); $^{13}$C NMR (100 MHz, CDCl$_3$): δ 129.7, 70.8, 66.7, 32.1, 30.0, 29.7, 29.6, 26.4, 22.9, 14.3.

<9-2> Synthesis of Compound 21

A compound 21 was synthesized with a yield of 89% according to the typical synthesis procedure for Upjohn dihydroxylation as described in Example 1-2'. $^1$H NMR (400 MHz, CDCl$_3$): δ 3.78 (br s, 2H), 3.61-3.57 (m, 4H), 3.47 (t, J=8 Hz, 4H), 2.89 (d, J=1.6 Hz, 2H), 1.62-1.54 (m, 4H), 1.40-1.26 (m, 32H), 0.88 (t, J=8 Hz, 6H); $^{13}$C NMR (100 MHz, CDCl$_3$): δ 72.2, 71.9, 71.3, 32.1, 29.8 (2C), 29.7, 29.5, 26.3, 22.9, 14.3.

<9-3> Synthesis of Compound 24

A compound 24 was synthesized with a yield of 86% according to the typical procedure for a glycosylation reaction as described in Example 1-3. $^1$H NMR (400 MHz, CDCl$_3$): δ 3.78 (br s, 2H), 3.61-3.57 (m, 4H), 3.47 (t, J=8 Hz, 4H), 2.89 (d, J=1.6 Hz, 2H), 1.62-1.54 (m, 4H), 1.40-1.26 (m, 32H), 0.88 (t, J=8 Hz, 6H); $^{13}$C NMR (100 MHz, CDCl$_3$): δ 72.2, 71.9, 71.3, 32.1, 29.8 (2C), 29.7, 29.5, 26.3, 22.9, 14.3.

<9-4> Synthesis of M-BTM-C11

M-BTM-C11 was synthesized with a yield of 94% according to the typical synthesis procedure for a deprotection reaction as described in Example 1-4. $^1$H NMR (400 MHz, CD$_3$OD): δ 5.16 (br s, 2H), 4.57 (d, J=4 Hz, 1H), 4.50 (d, J=8 Hz, 1H), 4.15-4.12 (m, 2H), 3.86-3.49 (m, 28H), 3.38-3.32 (m, 2H), 3.31-3.22 (m, 6H), 1.60-1.53 (m, 4H), 1.40-1.29 (m, 34H), 0.90 (t, J=8 Hz, 6H); $^{13}$C NMR (100 MHz, CD$_3$OD): δ 104.4, 104.2, 103.0 (2C), 81.4, 81.3, 79.6, 79.5, 77.8, 77.7 (2C), 76.7, 75.1, 75.0 (2C), 74.9, 74.2, 72.7, 72.6, 71.7, 71.5, 71.1, 62.8, 62.4, 62.3, 33.2, 31.0 (2C), 30.9 (3C), 30.8 (2C), 30.7, 27.5 (2C), 23.9, 14.7; HRMS (EI): calcd. for $C_{50}H_{94}O_{24}Na^+$ $[M+Na]^+$ 1101.6033, found 1101.6034.

<Experimental Example 1> Structures of BTMs

The structures of BTMs were distinct in terms of the stereochemistry in a linker region (FIG. 3). The design of BTMs has a characteristic in that two alkyl chains and two dimaltoside hydrophilic groups are linked via a butane-1,2,3,4-tetraol (BT) linker. Since two chiral centers are present in the BT linker (C2 and C3), three BTM stereoisomers (A-BTM, B-BTM, and M-BTM) may be synthesized. The BT linker for A-isomers includes a chiral center having 2S and 3S configurations, and the BT linker for B-isomers includes 2S and 3S configurations. Therefore, since hydrophobic groups of the A-/B-BTMs have a mirror-image relationship with each other, the A-/B-BTMs are enantiomers of each other. On the other hand, the BT linker having 2R and 3S (or 2S and 3R) configurations is used to prepare M-isomers. Therefore, there is a diastereomeric relationship between hydrophobic groups of the M-isomers and the A-/B-isomers. The M-isomer is a meso compound because planes of symmetry are present in the hydrophobic group of the M-isomer. Since a hydrophobic group of each of the A-/B-/M-BTMs is linked to two dimaltoside hydrophilic groups via a stereospecific β-glycosidic bond, all the compounds have a diastereomeric relationship due to different relative directionality of the hydrophobic and hydrophilic groups.

Also, the respective compounds had carbon chain lengths varying from C9 to C11 in each of the compounds, which were used to name the compounds. The A- and B-isomers were prepared by introducing two hydroxyl groups into α and 3 faces of an (E)-but-2-ene-1,4-diol derivative. The high stereospecificity of this reaction was achieved through the Sharpless asymmetric dihydroxylation well known in the art. On the other hand, the M-isomers were prepared from (Z)-but-2-ene-1,4-diol through Syn-dihydroxylation using $OsO_4$. The M-BTMs have advantages in synthesis over other isomers (A-/B-BTMs) because the M-BTMs may be prepared through a 4-step high-yield synthesis process. On the other hand, a lot of effort and costs are required to mass-produce two different isomers (A-/B-isomers). This is because an expensive AD-Mix-α/β reagent is used in a Sharpless asymmetric dihydroxylation process used in the step of introducing stereoselective chirality into the C2/C3 carbon, and a reaction time of 5 days was also required. In the synthesis protocol consisting of 4 steps required to prepare a final amphiphilic molecule, the entire yield was in a range of 50 to 60%.

The high diastereomeric purities of different isomers were confirmed through the $^1H$ NMR spectra of the different isomers (FIGS. 4A to 4C and FIG. 5). Hydrogen of the A- and B-isomers of the BTM-C9 attached to an anomeric carbon (C1) was designated "Ha." In this case, these respective hydrogen atoms were observed as doublets at 4.53 and 4.46 ppm on the $^1H$ HMR spectrum. On the other hand, in the case of the M-isomers, the central regions of the doublets had two separate peaks at 4.48 and 4.54 ppm, respectively.

Figure 5:
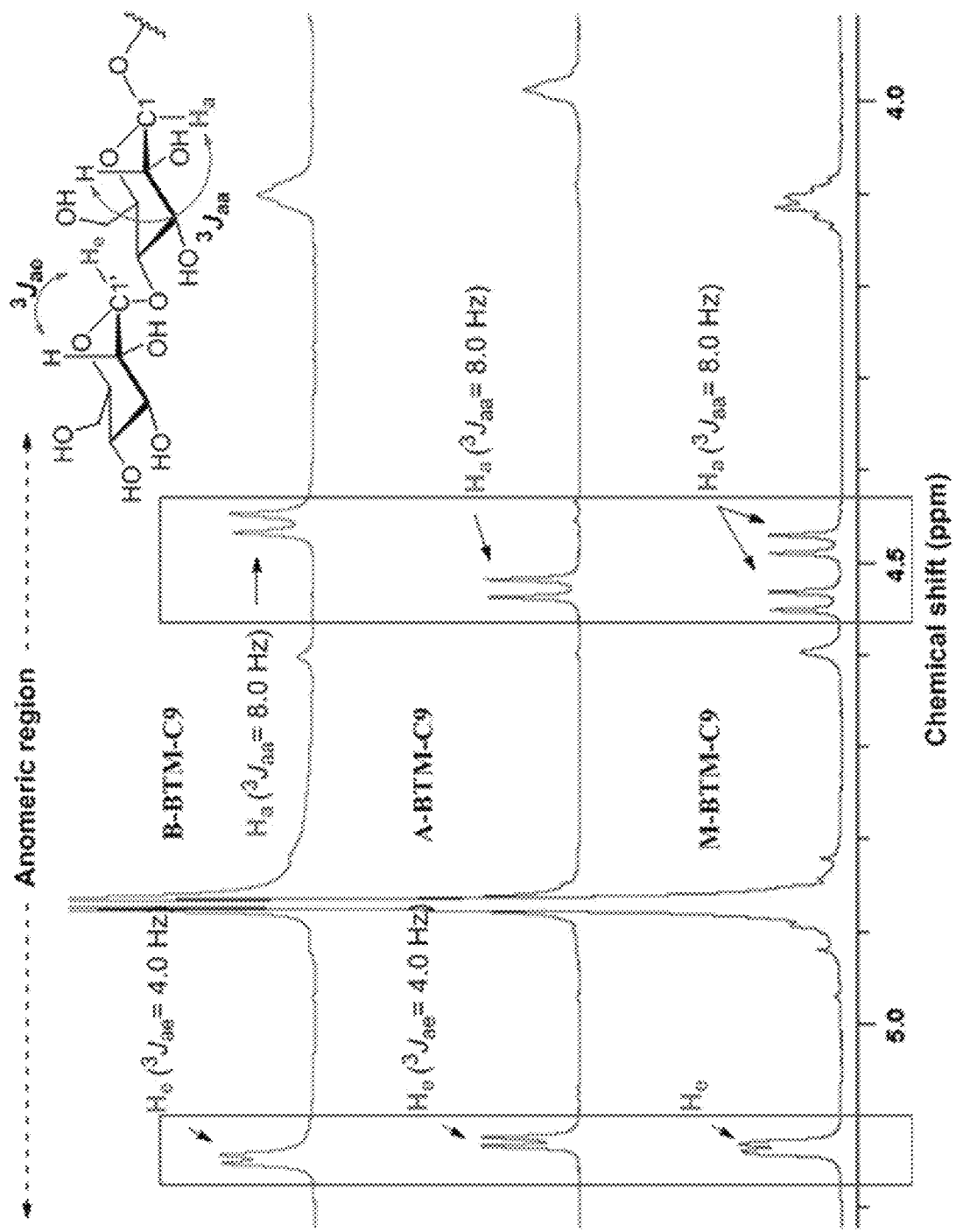
FIG. 5 is a diagram showing anomeric regions of the $^1H$ NMR spectrum with respect to the three BTM-C9 isomers.
Figure 7A:
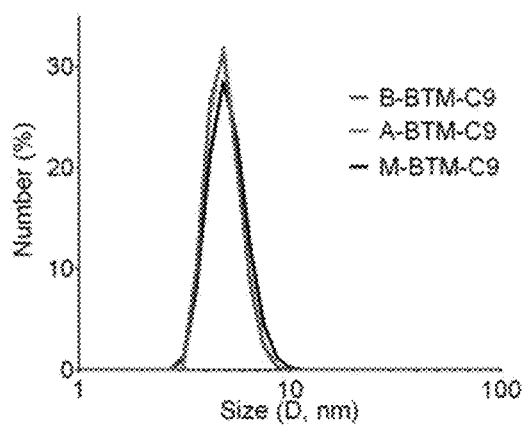
FIGS. 7A, 7B, 7C and 7D are diagrams showing a size distribution of micelles formed by BTMs.
Figure 7B:
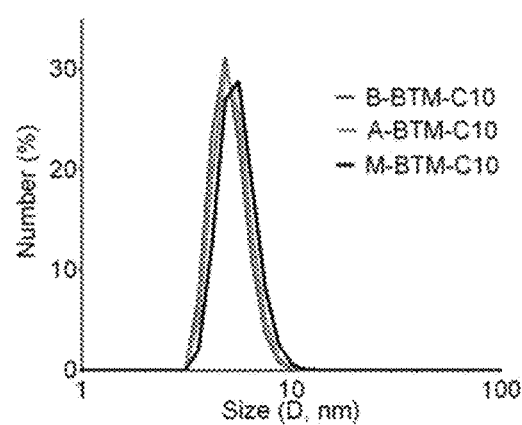
Figure 7C:
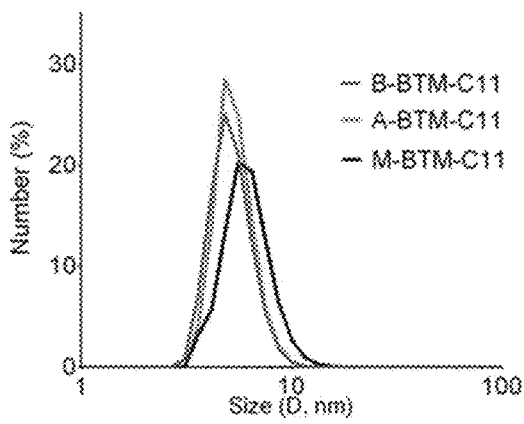
Figure 7D:
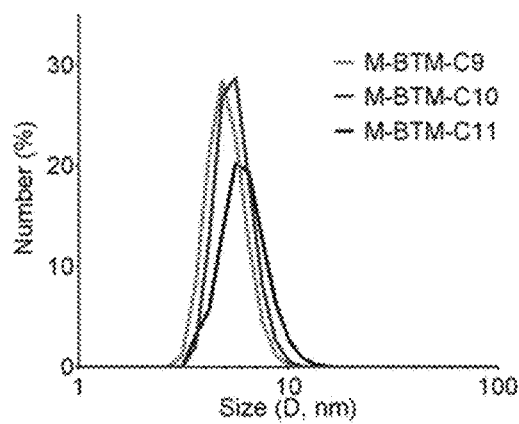

Also, considering that a coupling constant ($^3J$) of all the isomers to the anomeric hydrogen (Ha) was 8.0 Hz, it was revealed that the β-glycosidic bond was successfully formed in the glycosylation step. Since the α-glycosidic bond had a smaller coupling constant ($^3J=4.0$ Hz) with respect to the anomeric hydrogen, and peaks of the α-glycosidic bond was also positioned in the vicinity of 5.14 ppm, the anomeric hydrogen was clearly distinct from the anomeric hydrogen having the β-glycosidic bond. This was observed for hydrogen ($H_e$) attached to another anomeric carbon (C1') in all the BTM isomers (FIG. 5).

<Experimental Example 2> Characteristics of BTMs

To determine characteristics of the BTMs of Preparative Examples 1 to 9 synthesized according to the synthesis method of Example 1, the molecular weight (M.W.) and critical micelle concentration (CMC) of the BTMs, and the hydrodynamic radii (Rh) of the formed micelles were measured.

Specifically, the critical micelle concentration (CMC) was measured using diphenylhexatriene (DPH) as a fluorescent stain, and the hydrodynamic radii (Rh) of the micelles formed by each preparation (1.0% by weight) were measured through a dynamic light scattering (DLS) experiment. For comparison with DDM which is a conventional amphiphilic molecule (detergent), the measured results are listed in Table 1.

TABLE 1

| Detergents | M.W. | CMC (mM) | CMC (% by weight) | $R_h$ (nm) |
|---|---|---|---|---|
| B-BTM-C9 | 1023.2 | ~0.023 | ~0.0023 | 2.9 ± 0.04 |
| A-BTM-C9 | 1023.2 | ~0.021 | ~0.0022 | 2.9 ± 0.04 |
| M-BTM-C9 | 1023.2 | ~0.017 | ~0.0017 | 3.2 ± 0.05 |
| B-BTM-C10 | 1051.2 | ~0.013 | ~0.0014 | 3.1 ± 0.07 |
| A-BTM-C10 | 1051.2 | ~0.011 | ~0.0012 | 3.2 ± 0.07 |
| M-BTM-C10 | 1051.2 | ~0.008 | ~0.0009 | 3.5 ± 0.07 |
| B-BTM-C11 | 1079.3 | ~0.008 | ~0.0009 | 3.5 ± 0.08 |
| A-BTM-C11 | 1079.3 | ~0.007 | ~0.0008 | 3.5 ± 0.03 |
| M-BTM-C11 | 1079.3 | ~0.006 | ~0.0006 | 4.7 ± 0.27 |
| DDM | 510.1 | ~0.17 | ~0.0087 | 3.4 ± 0.03 |

The CMC values (0.023 to 0.006 mM) of all the BTMs were significantly lower than the CMC value (0.17 mM) of DDM. Therefore, it was revealed that the BTMs were able to have a similar or superior effect to DDM when used at a small amount since the micelles were easily formed when the BTMs were present at a low concentration. Also, the CMC values of the BTMs were reduced with an increase in the length of the alkyl chain from C9 to C11, which is determined to be due to increased hydrophobicity with an extension in the length of the alkyl chain. Among the three BTM stereoisomers, the M-isomers had the lowest CMC value, and the A-isomers had the second lowest CMC value. Since the three stereoisomers contain the same hydrophobic and hydrophilic groups (that is, the same hydrophile-lipophile balance), these results suggest that the stereoisomers have different tendencies in self-aggregation, depending on the stereochemistry thereof. The M-isomers had the highest tendency in self-aggregation, followed by the A-isomers and then the B-isomers.

The size of the micelles formed by the BTMs tended to increase with an increase in the length of the alkyl chain. There is a small difference in micelle size between the A-isomers and the B-isomers because there is an optically isomeric relationship between the hydrophobic groups. On the other hand, the M-isomers tended to form significantly larger micelles, compared to the other stereoisomers. This is because the M-isomers have a diastereomeric relationship with the hydrophobic groups of the other isomers.

It is judged that such distinct characteristics (a small CMC value and a large micelle size) of the M-isomers compared to those of the A- and B-isomers are based on changes in molecular structure of the other isomers in a water-soluble medium. In a gaseous state, each molecule assumes a staggered form between carbon substituents to form a dihedral angle of 60° between two alkyl chains and two dimaltoside hydrophilic groups (indicated by X and Y in FIG. 3, respectively). However, two alkyl chains of each isomer are subjected to a force which brings them closer to each other due to a hydrophobic effect in a water-soluble environment, resulting in a decreased dihedral angle (X) between the two alkyl chains. Such a decrease in the dihedral angle causes an increase in torsional/steric strain in molecules. Therefore, it is expected that two alkyl chains of an amphiphilic molecule dissolved in a water-soluble solution may adopt a compromise position between two opposing forces to form a dihedral angle (X) smaller than 60°. It is interesting to note that the decreased dihedral angle (X) causes different results in the relative orientation of the dimaltoside hydrophilic groups, depending on the stereochemistry of the isomers (A-/B-/M-isomers). Specifically, a decrease in the X dihedral angle causes a decrease in a dihedral angle (Y) between two hydrophilic groups in the M-isomers, but may rather cause an increase in the dihedral angle (Y) in the A-/B-isomers. As a result, the M-isomers adopt a structure having a relatively small dihedral angle in both X and Y, resulting in decreased volume of hydrophobic and hydrophilic moieties, compared to the other isomers. Such distinct characteristics of the M-isomers are expected to lead to more effective packing of micelles than the A- and B-isomers having a relatively large hydrophilic volume, and thus contribute positively to the stability of membrane proteins. Such structural characteristics have something to do with the relatively small CMC value and the formation of large micelles, as observed for the M-isomers. That is, the M-isomers form micelles having a large diameter since the M-isomers have a geometric structure closer to a cylindrical shape than those of the A- and B-isomers.

When the energy-minimized structure of each isomer was calculated at a level of B3LYP/6-31G using the density functional theory (DFT), the Y dihedral angle was lowest in the M-isomers (FIG. 6). In this calculation, the M-isomers had both X and Y dihedral angles smaller than 60°, and the A- and B-isomers had an X dihedral angle smaller than 60° and a Y dihedral angle larger than 60°. Such results of calculation support our hypothesis about relative movement of the alkyl chains and hydrophilic groups due to a hydrophobic effect in a water-soluble solution.

Meanwhile, when the size distribution of micelles formed by the BTM was examined through DLS, it was revealed that all the isomers had only one cluster of micelles, indicating that the micelles are highly homogeneous (FIG. 7).

From these results, it can be seen that the micelles were easily formed even when the BTMs of the present invention were used at a small amount because the BTMs had a lower CMC value than DDM, thus the BTMs had a much higher tendency to be self-assembled than DDM, the micelles formed by the BTM isomers had different sizes depending on the type of isomers, and the micelles formed by the BTMs were highly homogeneous.

<Experimental Example 3> Evaluation of Ability of BTMs to Stabilize Structure of UapA Membrane Protein A UapA protein is a uric acid-xanthine/$H^+$ symporter in *Aspergillus nidulans*. An experiment for measuring structural stability of a uric acid-xanthine/$H^+$ symporter (UapA) by BTMs in an aqueous solution was performed. The structural stability of UapA was measured using fluorescence size exclusion chromatography (FSEC).

Specifically, UapAG411V$_{A1-11}$ (hereinafter referred to as 'UapA') was expressed as a GFP fusion protein in a *Saccharomyces cerevisiae* FGY217 strain, and divided into a sample buffer (20 mM Tris (pH 7.5), 150 mM NaCl, 0.03% DDM, and 0.6 mM xanthine). This procedure was performed according to the method disclosed in the article by J. Leung et al. (*Mol. Membr. Biol.* 2013, 30, 32-42). Membranes containing UapA were re-suspended in PBS (10 mM imidazole pH 8.0, 150 mM NaCl, and 10% glycerol), and a concentration of proteins was measured. A concentration of the membranes was adjusted to 1 mg/mL, and 1 mL aliquots were incubated with a final concentration (1.0% by weight) of DDM or BTMs while being gently stirred at 40° C. for 10 minutes. 100 µL aliquots were removed from the respective tubes, and fluorescence reading on each sample was performed before and after the aliquots were ultracentrifuged at 150,000 g for 10 minutes to remove insoluble matter. Water-soluble fractions remaining under each condition were subjected to fluorescence SEC (FSEC) using a Superose 6 column (GE Healthcare) equilibrated with a buffer containing a proper preparation (DDM or BTM).

Figure 8A:
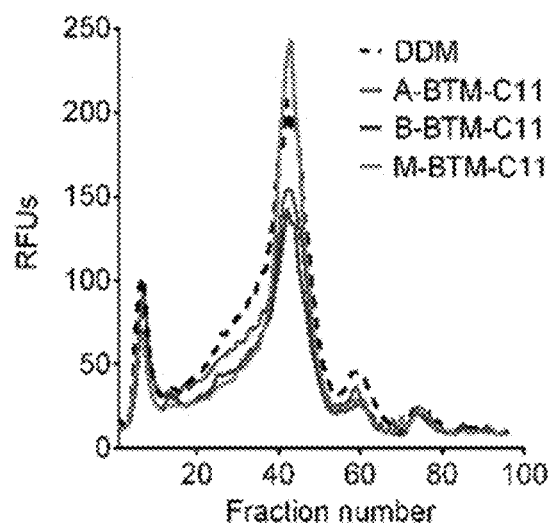
FIGS. 8A and 8B are diagrams showing results of measuring thermal stability of UapA by BTMs or DDM in an aqueous solution using fluorescence size exclusion chromatography (FSEC)
Figure 8B:
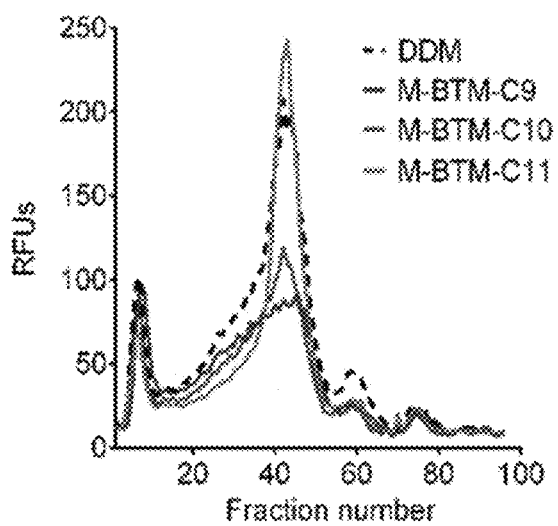

From the results shown in FIG. 8, it was revealed that the UapA extracted using DDM had a monodisperse peak with a relatively high strength (approximately fraction number of 40) even after the UapA was incubated at 40° C. for 10 minutes. This suggests that DDM is used to effectively extract proteins from cell membranes and the dissolved proteins are maintained in a relatively stable state. A significant increase in the recovery of monodisperse peaks was observed in the UapA solubilized with M-BTM-C11, compared to DDM and other isomers. Also, it was revealed that the M-isomer had a very excellent effect in maintaining the structural stability of the UapA protein due to the very narrow width of the monodisperse peaks, compared to the other isomers and DDM (FIG. 8A). In particular, it was confirmed that, among the M-BTMs, M-BTM-C11 having the longest alkyl chain length had the most excellent effect (FIG. 8B).

From these results, it can be seen that M-BTM-C11 was able to be effectively used to extract and stabilize the membrane proteins since the M-BTM-C11 had a superior effect in effectively extracting UapA from the cell membrane and maintaining UapA in a structurally stable state in an aqueous solution, compared to the A- and B-isomers.

<Experimental Example 4> Evaluation of Ability of BTMs to Stabilize Structure of LeuT Membrane Protein An experiment for measuring structural stability of a LeuT protein by BTMs in an aqueous solution was performed. Each amphiphilic compound was used at a concentration of (a) CMC+0.04% by weight or (b) CMC+0.2% by weight, and the ligand-binding characteristics of LeuT were determined through a scintillation proximity assay (SPA) using [$^3$H]-Leu. The measurement was performed at room temperature at regular intervals during an incubation period of 12 days.

Specifically, thermophilic bacteria (*Aquifex aeolicus*)-derived wild-type leucine transporter (LeuT) were purified using the method as described above (G. Deckert, et al., *Nature* 1998, 392, 353-358). LeuT was expressed in *E. coli* C41 (DE3) transformed with pET16b encoding a C-terminal 8×His-tagged transporter (an expression plasmid was provided from Dr. E. Gouaux, Vollum Institute, Portland, Oreg., USA). In summary, after a bacterial membrane is separated and solubilized in 1% (w/v) DDM, proteins were bound to a Ni$^{2+}$-NTA resin (Life Technologies, Denmark), and then eluted with 20 mM Tris-HCl (pH 8.0), 1 mM NaCl, 199 mM KCl, 0.05% (w/v) DDM, and 300 mM imidazole. Thereafter, the purified LeuT (approximately 1.5 mg/mL) was diluted tenfold with a buffer supplemented with BTMs or DDM at a final concentration of CMC+0.04% (w/v) or CMC+0.2% (w/v), except that DDM and imidazole were excluded from the same buffer. Protein samples were stored at room temperature for 12 days, and centrifuged for a given time, and the characteristics of the proteins were determined by measuring a [$^3$H]-leucine binding ability using SPA. SPA was performed with 5 µL of each of the protein samples in a buffer containing 200 mM NaCl and each BTM (or DDM). An SPA reaction was performed in the presence of 20 nM [$^3$H]-leucine and copper chelate (His-Tag) YSi beads (PerkinElmer, Denmark). The entire [$^3$H]-leucine binding affinity to each sample was measured using a MicroBeta liquid scintillation counter (PerkinElmer).

As shown in FIG. 9, it was revealed that all the BTM-C10 isomers had a much more superior effect in maintaining the ligand-binding characteristics of LeuT during an incubation period of 12 days, compared to DDM. That is, all the BTM-C10 isomers maintained the transporter ligand-binding characteristics intact for a long time even when present at a high compound concentration. On the other hand, the continuous structural collapse of the solubilized transporter was observed in DDM with an increasing compound concentration (FIG. 9A). When the concentration of the compound increased to CMC+0.2% by weight, there was a more distinct difference in an effect between the BTM-C10 compounds and DDM in stabilizing the transporter (FIG. 9B).

Also, as shown in FIGS. 10 and 11, there was no great difference in effect between the BTM isomers (A-/B-/M-/BTMs) in maintaining the characteristics of the transporter.

When the length of the alkyl chain increased to C11 or decreased C9, an effect of all the BTMs (BTM-C11s and BTM-C9s) to stabilize the proteins was slightly lower than that of the BTM-C10s. That is, it can be seen that the structures of BTMs having a C10 alkyl chain length was optimal for stabilization of LeuT. However, all the BTM isomers containing a C9 or C11 alkyl chain also had a superior effect to DDM, particularly had the same tendency when present at a compound concentration of CMC+0.2% by weight (FIGS. 10 and 11).

These results suggest that the entire structure of the BTMs is favorable for maintaining the structural stability of LeuT. Similar to the BTM-C10, all the BTM-C9 or BTM-C11 molecules showed very similar patterns between the stereoisomers with respect to the ligand-binding characteristics of LeuT. This indicates that LeuT was not greatly affected by a stereochemical difference between the BTM isomers unlike the UapA.

<Experimental Example 5> Evaluation of Ability of BTMs to Stabilize Structure of $\beta_2$AR Membrane Protein An experiment for determining the structural stability of a human $\beta_2$ adrenergic receptor ($\beta_2$AR) and a G-protein-coupled receptor (GPCR) by BTMs was performed. That is, a receptor purified with DDM was diluted with a buffer solution containing only each of the BTMs without cholesteryl hemisuccinate (CHS) or a buffer solution containing DDM with CHS. The final compound concentration was CMC+0.2% by weight, and the ligand-binding characteristics of the receptor were determined through [$^3$H]-dihydroalprenolol ([$^3$H]-DHA) binding.

Specifically, a radioactive ligand binding test was performed using the following method. $\beta_2$AR was purified with 0.1% DDM (D. M. Rosenbaum et al., *Science*, 2007, 318, 1266-1273.), and finally concentrated to approximately 10 mg/mL (approximately 200 µM). A master binding mixture containing 10 nM [$^3$H]-dihydroalprenolol (DHA) supplemented with 0.5 mg/mL BSA in each 0.2% amphiphilic compound (DDM or BTMs) was prepared using the $\beta_2$AR purified with DDM. The ligand-binding characteristics of the receptor purified with the amphiphilic compound at 0.2 pmol was monitored at regular intervals while the receptor was incubated at room temperature for 3 days. The ligand-binding characteristics of the receptor were determined using a water-soluble radioactive ligand binding assay as will be described below. The receptor purified with DDM or each of the BTMs was incubated with 10 nM [$^3$H]-DHA at room temperature for 30 minutes. The mixture was loaded on a G-50 column, and flow-through fractions were collected using 1 mL of a binding buffer (20 mM HEPES (pH 7.5) supplemented with 0.5 mg/mL BSA and 20×CMC of each amphiphilic compound, 100 mM NaCl). Then, the G-50 column was filled with 15 mL of a scintillation fluid. Receptor-bound [$^3$H]-DHA was counted using a scintillation counter (Beckman). Non-specific binding of [$^3$H]-DHA was determined by adding 2 µM of alprenolol (Sigma) in the same binding reaction. The binding affinity of [$^3$H]-DHA was plotted on a column graph, and each experiment was performed in triplicate.

As shown in FIG. 12, the BTM-C11 compounds had a superior effect in maintaining the ligand-binding characteristics of the receptor, compared to the BTM-C10 compounds, and the BTM-C11 compounds were also nearly similar in performance to DDM. Also, the A- and M-isomers had similar effects with respect to each other, and had a superior effect with respect to the B-isomers (FIGS. 12A and 12B). It was judged that a slight decrease in the ligand-binding characteristics of the receptor observed for A-BTM-C11 or M-BTM-C11 compared to DDM is based on the absence of CHS known to enhance the stability of GPCRs.

Also, the ligand-binding characteristics of the receptor dissolved in A-BTM-C11, M-BTM-C11 or DDM were monitored at regular intervals while the receptor was incubated at room temperature for 3 days. The results are shown in FIG. 12C. As a result, it was revealed that the receptor solubilized with DDM initially had a high ability to bind to a ligand, but the binding characteristics of the receptor were drastically lost, and eventually only 10% of the initial binding ability remained after 3 days of incubation. On the other hand, the receptor solubilized with M-BTM-C11 had initial ligand-binding characteristics similar to those of the receptor solubilized with DDM, but the ligand-binding characteristics of the receptor were maintained at approximately 70% of an initial ligand-binding ability after 3 days of incubation (FIG. 12C). M-BTM-C11 had a very high effect in stabilizing the receptor even with the absence of CHS, compared to DDM. Also, it judged that an effect of the amphiphilic compounds on the stability of the receptor ($\beta_2$AR) is determined in the order of M-BTMs>A-BTMs>B-BTMs.

Therefore, it can be seen that, among the BTMs, M-BTM-C11 especially had a much more superior effect in maintaining the long-term stability of $\beta_2$AR, compared to DDM.

<Experimental Example 6> Evaluation of Ability of BTMs to Stabilize Structure of MelB Membrane Protein The BTM-C11s exhibiting excellent effects in the experiments on UapA, LeuT and $\beta_2$AR were selected to perform an experiment for determining the structural stability of a *Salmonella typhimurium* melibiose permease (MelB) protein by BTM-C11s. The MelB protein was extracted from a membrane using BTM-C11s or DDM, and the amount and structure of the extracted protein were analyzed through SDS-PAGE and Western Blotting. A concentration of the amphiphilic compound used was 1.5% by weight, and the protein was extracted at four temperatures (0, 45, 55, and 65° C.), and incubated at the same temperature for 90 minutes. Thereafter, an amount of the protein remaining dissolved in an aqueous solution was measured to evaluate two types of performance: protein extraction efficiency and stabilization ability of the compound. The amount of the protein extracted and stabilized with each of the amphiphilic molecules is expressed as a relative value (%) of the entire amount of proteins contained in a membrane sample which is not treated with the amphiphilic molecules.

Specifically, *Salmonella typhimurium* melibiose permease (MelB$_{St}$) having a 10-His tag at the C-terminus thereof was expressed in *E. coli* DW2 cells (AmelB and AlacZY) using a plasmid pK95ΔAHB/WT MelB$_{St}$/CH10. Cell growth and membrane preparation were performed according to the method disclosed in the article by A. S. Ethayathulla et al. (*Nat. Commun.* 2014, 5, 3009). A protein assay was performed using a Micro BCA kit (Thermo Scientific, Rockford, Ill.). An effect of the isomers (A-BTM-C11, B-BTM-C11, and M-BTM-C11) of the BTM-C11s or DDM on the MelB$_{St}$ stability was evaluated using the protocol disclosed in P. S. Chae et al. (*Nat. Methods* 2010, 7, 1003-1008). A membrane sample (having a final protein concentration of 10 mg/mL) containing MelB$_{St}$ was incubated at four temperatures (0, 45, 55, and 65° C.) for 90 minutes in a solubilizing buffer (20 mM sodium phosphate, pH 7.5, 200 mM NaCl, 10% glycerol, and 20 mM melibiose) containing 1.5% (w/v) DDM or the BTM-C11 isomers. To remove insoluble matter, the sample was ultracentrifuged at 355,590 g at 4° C. for 45 minutes using a Beckman Optima™ MAX ultracentrifuge equipped with a TLA-100 rotor. The dissolved fraction was separated by 16% SDS-PAGE, and then immunoblotted with a Penta-His-HRP antibody (Qiagen, Germantown, Md.). The membrane fraction containing 20 μg of untreated proteins was used to represent the entire MelB, and the treated samples were loaded in each well at the same volume. MelB$_{St}$ was measured by an ImageQuant LAS 4000 Biomolecular imager (GE Health Care Life Sciences) using a SuperSignal West Pico chemiluminescent substrate.

From the results as shown in FIG. 13, it was revealed that DDM had high MelB protein extraction efficiency at 0° C. The three BTM isomers had similar protein extraction efficiency, but had a slightly lower efficiency of extracting the proteins from membranes at a low temperature, compared to DDM.

However, when the temperature increased to 45° C., all the BTM isomers had an effect of effectively extracting the MelB protein, and had a level of MelB solubility similar to DDM. Among the steric isomers, the M-isomers had the best effect at this temperature.

When the temperature increased to 55° C., a greater difference between the M-isomers and the A-/B-isomers was observed. It can be seen that MelB solubilized with M-BTM-C11 exhibited complete solubility even at this high temperature, but an amount of the protein solubilized with the A- or B-isomers drastically decreased. Since the extraction efficiency of DDM was further reduced at this temperature, an amount of the protein remaining dissolved in an aqueous solution accounted for only approximately 15% of the extracted protein.

The superiority of the M-isomers to DDM and two other isomers was determined by solubilizing MelB at 65° C. In this case, a detectable level of dissolved MelB was confirmed only when extracted with the M-isomers, and a very small amount of the protein remained when extracted with the other isomers or DDM.

From these results, it can be seen that the BTM-C11 isomer of the present invention had an ability to extract a level of the MelB protein similar to DDM at a low temperature, and had a superior effect of solubilizing and stabilizing the MelB protein at a high temperature of 45, 55 and 65° C., compared to DDM.

When the butane-tetraol-based compound according to the exemplary embodiments of the present invention is used, a membrane protein can be stably stored in an aqueous solution for a long time, compared to the conventional compounds, and thus can be used to analyze the function and structure of the membrane protein.

The analysis of the structure and function of the membrane protein is applicable to studies on protein structures which are closely associated with the development of new drugs since the analysis of the structure and function of the membrane protein is one of the fields which have received the most attention in biology and chemistry.

Since the compound according to the exemplary embodiments of the present invention is a chiral stereoisomer obtained by introducing hydrophobic and hydrophilic groups into a central structure exhibiting chirality, the characteristics of the compounds and the stabilizing characteristics of a membrane protein can vary depending on the types of stereoisomers. Such chirality of the amphiphilic compound can play an important role in stabilization and crystallization of the membrane protein.

Also, since the compound according to the exemplary embodiments of the present invention has a reduced size when the compound forms a complex with a membrane protein, high-quality crystals of the membrane protein can be obtained, thereby promoting crystallization of the membrane protein.

Further, the compound according to the exemplary embodiments of the present invention can be mass-produced for membrane protein research since the compound can be synthesized from easily available starting materials using a simple method.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A compound represented by the following Formula 1:

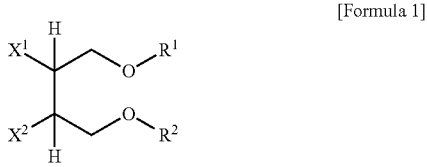

[Formula 1]

wherein $R^1$ and $R^2$ are each independently an unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group; and $X^1$ and $X^2$ are each independently a saccharide linked via oxygen, wherein the saccharide is glucose or maltose.

2. The compound of claim 1, wherein $R^1$ and $R^2$ are each independently an unsubstituted $C_3$-$C_{30}$ alkyl group; and $X^1$ and $X^2$ are each independently maltose linked via oxygen.

3. The compound of claim 1, wherein the compound of Formula 1 has a stereochemical configuration represented by one of the following Formulas 1a to 1c:

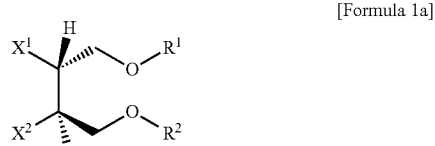

[Formula 1a]

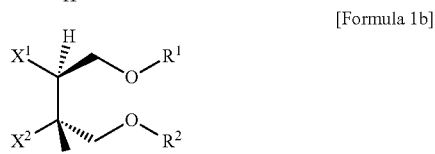

[Formula 1b]

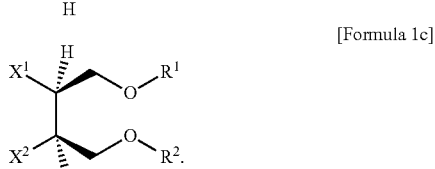

[Formula 1c]

4. The compound of claim 1, wherein the compound is one of the following Formulas 2 to 10:

[Formula 2]
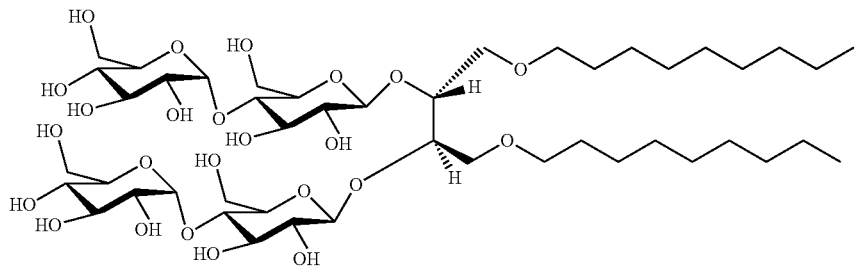
[Formula 3]
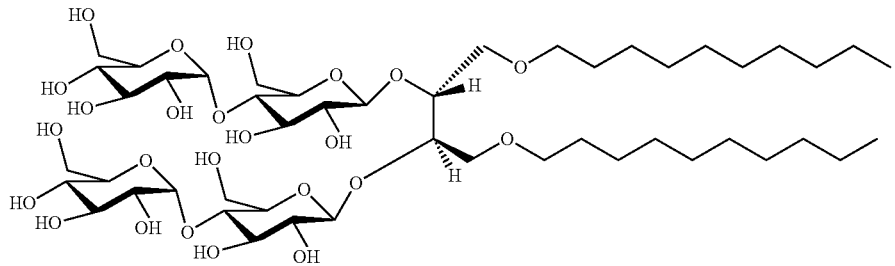
[Formula 4]
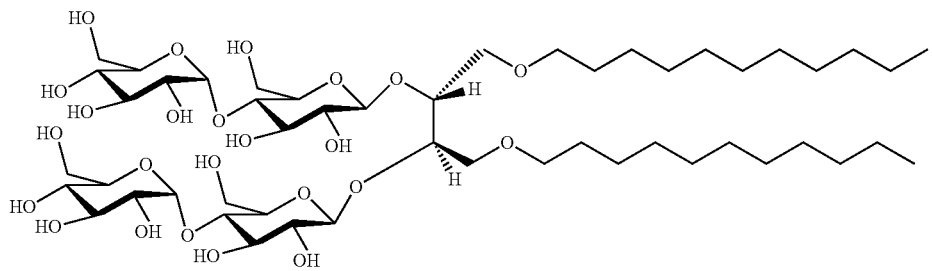
[Formula 5]
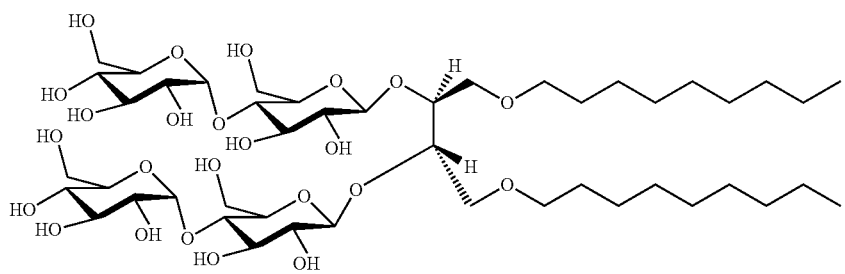
[Formula 6]
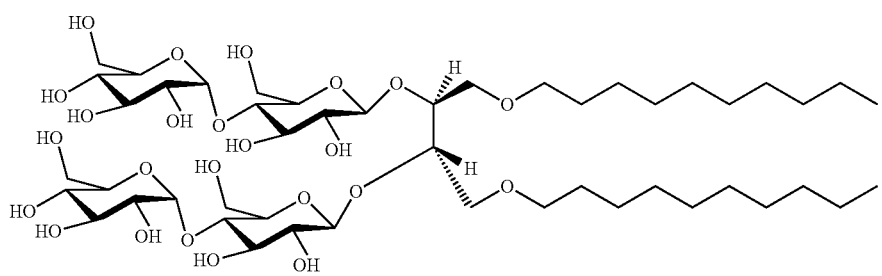
[Formula 7]
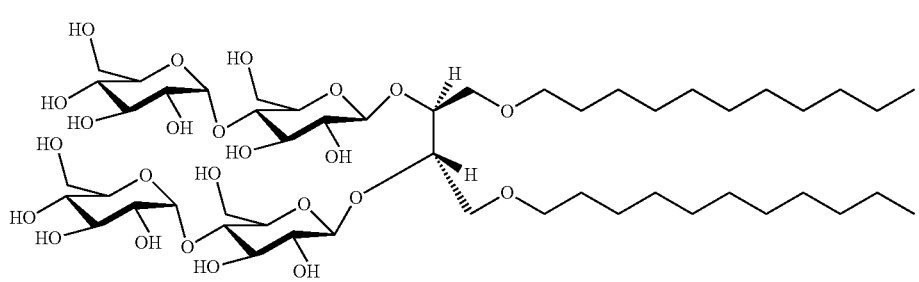

-continued

[Formula 8]

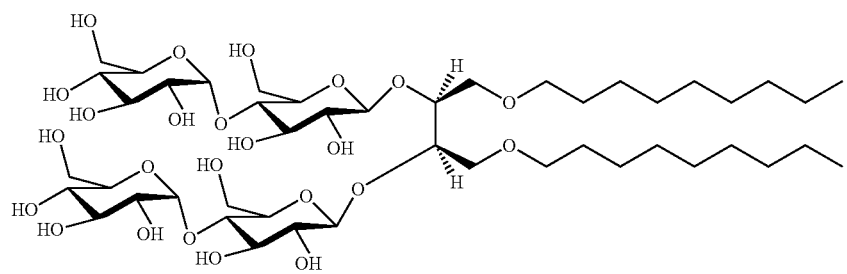

[Formula 9]

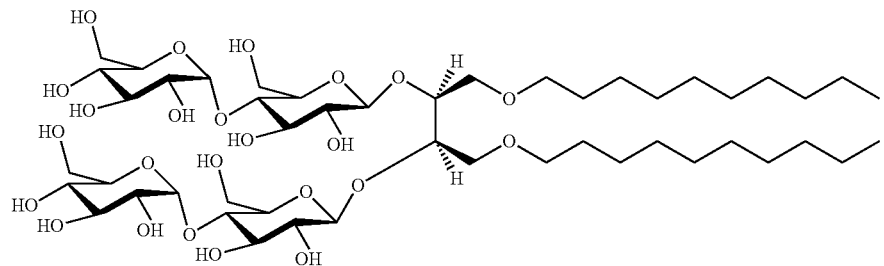

[Formula 10]

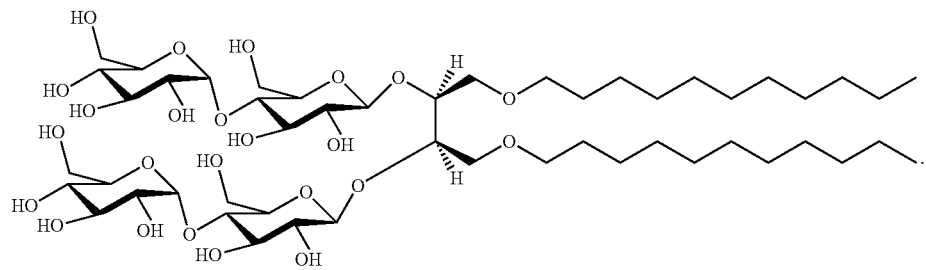

5. The compound of claim 1, wherein the compound is an amphiphilic molecule for extracting, solubilizing, stabilizing, crystallizing or analyzing a membrane protein.

6. The compound of claim 1, wherein the compound has a critical micelle concentration (CMC) of 0.0001 to 1 mM when present in an aqueous solution.

7. A composition for extracting, solubilizing, stabilizing, crystallizing or analyzing a membrane protein, comprising the compound defined in claim 1.

8. The composition of claim 7, wherein the composition is a micelle, liposome, emulsion or nanoparticle formulation.

9. A method of preparing a compound represented by the following Formula 1, comprising:
   1) performing a dialkylation reaction on (E)-but-2-ene-1,4-diol or (Z)-but-2-ene-1,4-diol to introduce an alkyl group;
   2) performing a dihydroxylation reaction on the product of step 1) to synthesize a diol compound;
   3) performing a glycosylation reaction on the product of step 2) to introduce a said saccharide to which a protective group is attached; and
   4) performing a deprotection reaction on the product of step 3):

[Formula 1]

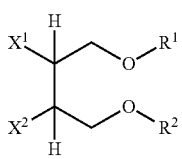

wherein $R^1$ and $R^2$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group; and $X^1$ and $X^2$ are each independently a saccharide linked via oxygen, wherein the saccharide is glucose or maltose.

10. The method of claim 9, wherein $R^1$ and $R^2$ are each independently a substituted or unsubstituted $C_3$-$C_{30}$ alkyl group; and $X^1$ and $X^2$ are each independently maltose linked via oxygen.

11. The method of claim 9, wherein the dihydroxylation of step 2) is Sharpless asymmetric dihydroxylation or Upjohn dihydroxylation.

12. A method of extracting, solubilizing, stabilizing, crystallizing or analyzing a membrane protein, comprising:
   treating a membrane protein with the compound represented by the following Formula 1 in an aqueous solution:

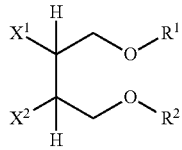

[Formula 1]

wherein $R^1$ and $R^2$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group; and $X^1$ and $X^2$ are each independently a saccharide linked via oxygen, wherein the saccharide is glucose or maltose.

13. The method of claim 12, wherein $R^1$ and $R^2$ are each independently a substituted or unsubstituted $C_3$-$C_{30}$ alkyl group; and $X^1$ and $X^2$ are each independently maltose linked via oxygen.

14. The method of claim 12, wherein the membrane protein comprises a uric acid-xanthine/$H^+$ symporter (UapA), a leucine transporter (LeuT), a human $\beta_2$ adrenergic receptor ($\beta_2$AR), a melibiose permease (MelB), or a combination of two or more types thereof.

* * * * *